United States Patent
Harris et al.

(10) Patent No.: US 9,856,481 B2
(45) Date of Patent: Jan. 2, 2018

(54) MICRORNA TREATMENT OF FIBROSIS

(71) Applicant: ANN AND ROBERT H. LURIE CHILDREN'S HOSPITAL OF CHICAGO, Chicago, IL (US)

(72) Inventors: Ann Harris, Chicago, IL (US); Lindsay R. Stolzenburg, Chicago, IL (US)

(73) Assignee: Ann & Robert H. Lurie Children's Hospital, Chicago, IL (US)

( * ) Notice: Subject to any disclaimer, the term of this patent is extended or adjusted under 35 U.S.C. 154(b) by 0 days.

(21) Appl. No.: 15/235,682

(22) Filed: Aug. 12, 2016

(65) Prior Publication Data

US 2017/0067061 A1 Mar. 9, 2017

Related U.S. Application Data

(60) Provisional application No. 62/204,782, filed on Aug. 13, 2015.

(51) Int. Cl.
  *C12N 15/113* (2010.01)
  *A61K 48/00* (2006.01)

(52) U.S. Cl.
  CPC .... *C12N 15/1138* (2013.01); *C12N 2310/141* (2013.01); *C12N 2320/30* (2013.01)

(58) Field of Classification Search
  None
  See application file for complete search history.

(56) References Cited

U.S. PATENT DOCUMENTS

| | | |
|---|---|---|
| 5,705,385 A | 1/1998 | Bally et al. |
| 5,965,542 A | 10/1999 | Wasan et al. |
| 6,287,591 B1 | 9/2001 | Semple et al. |
| 7,101,995 B2 | 9/2006 | Lewis et al. |
| 7,220,400 B2 | 5/2007 | Monahan et al. |
| 2005/0008617 A1 | 1/2005 | Chen et al. |
| 2005/0008689 A1 | 1/2005 | Semple et al. |
| 2005/0014962 A1 | 1/2005 | Gebeyehu et al. |
| 2005/0064595 A1 | 3/2005 | MacLachlan et al. |
| 2006/0008910 A1 | 1/2006 | MacLachlan et al. |
| 2006/0051405 A1 | 3/2006 | MacLachlan et al. |
| 2006/0083780 A1 | 4/2006 | Heyes et al. |
| 2007/0172950 A1 | 7/2007 | Wheeler et al. |
| 2007/0173476 A1 | 7/2007 | Leake et al. |
| 2015/0337332 A1* | 11/2015 | Ruohoa-Baker ......... C12N 9/22 514/44 R |
| 2016/0017321 A1* | 1/2016 | Zhang .................. C12N 15/111 514/44 A |

OTHER PUBLICATIONS

Das et al (Am J Respir Cell Mol Biol 50(5): 882-892, 2014).*
Akhurst et al (Nature Reviews Drug discovery 11:790-811, 2012).*
Anscher et al (Int. J. Radiation Oncology Biol. Phys, 71(3): 829-837, 2008).*
Yanagita et al (Nephrol Dial Transplant (2012) 27: 3686-3691).*
Lewis et al (Cell 120:15-20, 2005).*
Alexiou et al., Lost in translation: an assessment and perspective for computational microRNA target identification. Bioinformatics. Dec. 1, 2009;25(23):3049-55.
Arkwright et al., TGF-beta(1) genotype and accelerated decline in lung function of patients with cystic fibrosis. Thorax. Jun. 2000;55(6):459-62.
Bader et al., The promise of microRNA replacement therapy. Cancer Res. Sep. 15, 2010;70(18):7027-30.
Bhattacharyya et al., Elevated miR-155 promotes inflammation in cystic fibrosis by driving hyperexpression of interleukin-8. J Biol Chem. Apr. 1, 2011;286(13):11604-15.
Bhattacharyya et al., Relief of microRNA-mediated translational repression in human cells subjected to stress. Cell. Jun. 16, 2006;125(6):1111-24.
Celedón et al.,The transforming growth factor-betal (TGFB1) gene is associated with chronic obstructive pulmonary disease (COPD). Hum Mol Genet. Aug. 1, 2004;13(15):1649-56.
Chen et al., Solexa sequencing identification of conserved and novel microRNAs in backfat of Large White and Chinese Meishan pigs. PLoS One. 2012;7(2):e31426.
Cozens et al., CFTR expression and chloride secretion in polarized immortal human bronchial epithelial cells. Am J Respir Cell Mol Biol. Jan. 1994;10(1):38-47.
Dannemann et al., Annotation of primate miRNAs by high throughput sequencing of small RNA libraries. BMC Genomics. Mar. 27, 2012;13:116.
Dorfman et al., Complex two-gene modulation of lung disease severity in children with cystic fibrosis. J Clin Invest. Mar. 2008;118(3):1040-9.
Drumm et al., Genetic modifiers of lung disease in cystic fibrosis. N Engl J Med. Oct. 6, 2005;353(14):1443-53.
Feng et al., Selective miRNA expression profile in chronic myeloid leukemia K562 cell-derived exosomes. Asian Pac J Cancer Prev. 2013;14(12):7501-8.
Fogh et al., One hundred and twenty-seven cultured human tumor cell lines producing tumors in nude mice. J Natl Cancer Inst. Jul. 1997;59(1):221-6.
Fossum et al., Ets homologous factor regulates pathways controlling response to injury in airway epithelial cells. Nucleic Acids Res. Dec. 16, 2014;42(22):13588-98.
Friedman et al., Therapy for fibrotic diseases: nearing the starting line. Sci Transl Med. Jan. 9, 2013;5(167):1675r1.
Giard et al., In vitro cultivation of human tumors: establishment of cell lines derived from a series of solid tumors. J Natl Cancer Inst. Nov. 1973;51(5):1417-23.
Gillen et al., MicroRNA regulation of expression of the cystic fibrosis transmembrane conductance regulator gene. Biochem J. Aug. 15, 2011;438(1):25-32.
Glazov et al., Repertoire of bovine miRNA and miRNA-like small regulatory RNAs expressed upon viral infection. PLoS One. Jul. 27, 2009;4(7):e6349.

(Continued)

*Primary Examiner* — Richard A Schnizer
(74) *Attorney, Agent, or Firm* — Casimir Jones SC; David W. Staple

(57) ABSTRACT

Provided herein are microRNAs that target transforming growth factor beta (TGF-β) receptors and attenuate pathways of fibrosis. In particular, microRNA-1343 reduces expression of TGFBR1 and TGFBR2, decreases TGF-β signaling, represses pathways of fibrosis, and treats fibrotic diseases.

9 Claims, 30 Drawing Sheets

(56) References Cited

OTHER PUBLICATIONS

Harris et al., Transforming growth factor-beta(1) in bronchoalveolar lavage fluid from children with cystic fibrosis. Pediatr Pulmonol. Nov. 2009;44(11):1057-64.
Huan et al., RNA trafficking by acute myelogenous leukemia exosomes. Cancer Res. Jan. 15, 2013;73(2):918-29.
Huang et al., Bioinformatics enrichment tools: paths toward the comprehensive functional analysis of large gene lists. Nucleic Acids Res. Jan. 2009;37(1):1-13.
Huang et al., Systematic and integrative analysis of large gene lists using David bioinformatics resources. Nat Protoc. 2009;4(1):44-57.
Jiang et al.,miR2Disease: a manually curated database for microRNA deregulation in human disease. Nucleic Acids Res. Jan. 2009;37(Database issue):D98-104.
Kasai et al., TGF-beta1 induces human alveolar epithelial to mesenchymal cell transition (EMT). Respir Res. Jun. 9, 2005;6:56.
Kozomara et al., miRBase: annotating high confidence microRNAs using deep sequencing data. Nucleic Acids Res. Jan. 2014;42(Database issue):D68-73.
Lagraoui et al., Enhancement of human neutrophil survival and activation by TGF-beta 1. Cell Mol Biol (Noisy-le-grand). May 1997;43(3):313-8.
Leask et al., TGF-beta signaling and the fibrotic response. FASEB J. May 2004;18(7):816-27.
Leir et al., Inflammatory cytokines can enhance CD44-mediated airway epithelial cell adhesion independently of CD44 expression. Am J Physiol Lung Cell Mol Physiol. Dec. 2003;285(6):L1305-11.
Leung et al., Quantitative analysis of Argonaute protein reveals microRNA-dependent localization to stress granules. Proc Natl Acad Sci U S A. Nov. 28, 2006;103(48):18125-30.
Lewis et al., Conserved seed pairing, often flanked by adenosines, indicates that thousands of human genes are microRNA targets. Cell. Jan. 14, 2005;120(1):15-20.
Li et al., Alterations in microRNA expression in stress-induced cellular senescence. Mech Ageing Dev. Nov.-Dec. 2009;130(11-12):731-41.
Li et al., Therapeutic targeting of microRNAs: current status and future challenges. Nat Rev Drug Discov. Aug. 2014;13(8):622-38.
Liu et al., miR-21 mediates fibrogenic activation of pulmonary fibroblasts and lung fibrosis. J Exp Med. Aug. 2, 2010;207(8):1589-97.
Lu et al., MicroRNA expression profiles classify human cancers. Nature. Jun. 9, 2005;435(7043):834-8.
Mak et al., Elevated plasma TGF-beta1 levels in patients with chronic obstructive pulmonary disease. Respir Med. Jul. 2009;103(7):1083-9.
Megiorni et al., Elevated levels of miR-145 correlate with SMAD3 down-regulation in cystic fibrosis patients. J Cyst Fibros. Dec. 2013;12(6):797-802.
Meunier et al., Birth and expression evolution of mammalian microRNA genes. Genome Res. Jan. 2013;23(1):34-45.
Montgomery et al., MicroRNA mimicry blocks pulmonary fibrosis. EMBO Mol Med. Sep. 19, 2014;6(10):1347-56.
Pandit et al., Inhibition and role of let-7d in idiopathic pulmonary fibrosis. Am J Respir Crit Care Med. Jul. 15, 2010;182(2):220-9.
Persson et al., Identification of new microRNAs in paired normal and tumor breast tissue suggests a dual role for the ERBB2/Her2 gene. Cancer Res. Jan. 1, 2011;71(1):78-86.
Piriyapongsa et al., Origin and evolution of human microRNAs from transposable elements. Genetics. Jun. 2007;176(2):1323-37.
Pirkmajer et al., Serum starvation: caveat emptor. Am J Physiol Cell Physiol. Aug. 2011;301(2):C272-9.
Pottier et al., Identification of keratinocyte growth factor as a target of microRNA-155 in lung fibroblasts: implication in epithelial-mesenchymal interactions. PLoS One. Aug. 24, 2009;4(8):e6718.
Rackley et al., Building and maintaining the epithelium of the lung. J Clin Invest. Aug. 2012;122(8):2724-30.
Roberts et al., Transforming growth factor type beta: rapid induction of fibrosis and angiogenesis in vivo and stimulation of collagen formation in vitro. Proc Natl Acad Sci U S A. Jun. 1986;83(12):4167-71.
Santana et al., Increased expression of transforming growth factor beta isoforms (beta 1, beta 2, beta 3) in bleomycin-induced pulmonary fibrosis. Am J Respir Cell Mol Biol. Jul. 1995;13(1):34-44.
Scholand et al., Use of a genealogical database demonstrates heritability of pulmonary fibrosis. Lung. Oct. 2013;191(5):475-81.
Shi et al., Mechanisms of TGF-beta signaling from cell membrane to the nucleus. Cell. Jun. 13, 2003;113(6):685-700.
Silverman et al., Variability of pulmonary function in alpha-1-antitrypsin deficiency: clinical correlates. Ann Intern Med. Dec. 15, 1989;111(12):982-91.
Simone et al., Ionizing radiation-induced oxidative stress alters miRNA expression. PLoS One. Jul. 27, 2009;4(7):e6377.
Suzuki et al., Modulation of microRNA processing by p53. Nature. Jul. 23, 2009;460(7254):529-33.
Takeshita et al., Systemic delivery of synthetic microRNA-16 inhibits the growth of metastatic prostate tumors via downregulation of multiple cell-cycle genes. Mol Ther. Jan. 2010;18(1):181-7.
Trapnell et al., Differential gene and transcript expression analysis of RNA-seq experiments with TopHat and Cufflinks. Nat Protoc. Mar. 1, 2012;7(3):562-78.
Vanscoy et al., Heritability of lung disease severity in cystic fibrosis. Am J Respir Crit Care Med. May 15, 2007;175(10):1036-43.
Wiggins et al., Development of a lung cancer therapeutic based on the tumor suppressor microRNA-34. Cancer Res. Jul. 15, 2010;70(14):5923-30.
Willis et al., Induction of epithelial-mesenchymal transition in alveolar epithelial cells by transforming growth factor-beta1: potential role in idiopathic pulmonary fibrosis. Am J Pathol. May 2005;166(5):1321-32.
Wrana et al., TGF beta signals through a heteromeric protein kinase receptor complex. Cell. Dec. 11, 1992;71(6):1003-14.
Wright et al., Genome-wide association and linkage identify modifier loci of lung disease severity in cystic fibrosis at 11p13 and 20q13.2. Nat Genet. Jun. 2011;43(6):539-46.
Wu et al., Transforming growth factor-beta1 genotype and susceptibility to chronic obstructive pulmonary disease. Thorax. Feb. 2004;59(2):126-9.
Wynn, Integrating mechanisms of pulmonary fibrosis. J Exp Med. Jul. 4, 2011;208(7):1339-50.
Xiao et al., miR-29 inhibits bleomycin-induced pulmonary fibrosis in mice. Mol Ther. Jun. 2012;20(6):1251-60.
Yang et al., miR-145 regulates myofibroblast differentiation and lung fibrosis. FASEB J. Jun. 2013;27(6):2382-91.

* cited by examiner

| microRNA | Context Score | | Sum |
| --- | --- | --- | --- |
| | TGFBR1 3' UTR | TGFBR2 3' UTR | |
| miR-1343 | -0.9 | -0.39 | -1.29 |
| miR-665 | -0.61 | -0.42 | -1.03 |
| miR-2447/4646-5p | -0.81 | -0.21 | -1.02 |
| miR-4252 | -0.57 | -0.29 | -0.86 |
| miR-130ac/301ab | -0.16 | -0.65 | -0.81 |
| miR-1912 | -0.33 | -0.44 | -0.77 |
| miR-940 | -0.31 | -0.44 | -0.75 |
| miR-3144-5p | -0.53 | -0.13 | -0.66 |
| miR-3943 | -0.27 | -0.38 | -0.65 |
| miR-5095 | -0.28 | -0.36 | -0.64 |
| miR-361-3p | -0.44 | -0.18 | -0.62 |
| miR-145 | -0.29 | -0.28 | -0.57 |

FIG. 2A

| Gene | Number of miR-1343 sites | Context score |
|---|---|---|
| TGFBR1 | 3 | -0.90 |
| ELMO2 | 5 | -0.89 |
| SOX10 | 5 | -0.76 |
| COL5A1 | 4 | -0.70 |
| SPRED1 | 4 | -0.68 |
| ITGA5 | 4 | -0.62 |
| TGFBR2 | 1 | -0.39 |
| EGFR | 2 | -0.34 |
| SMURF1 | 2 | -0.28 |
| SMAD2 | 2 | >-0.02 |

FIG. 3G

| Term | Count | P-value |
|---|---|---|
| GO:0042127~regulation of cell proliferation | 57 | 8.26E-07 |
| GO:0070161~anchoring junction | 21 | 3.16E-06 |
| GO:0016323~basolateral plasma membrane | 23 | 3.33E-06 |
| GO:0040008~regulation of growth | 31 | 6.49E-06 |
| GO:0030055~cell-substrate junction | 16 | 9.79E-06 |
| GO:0005912~adherens junction | 19 | 9.99E-06 |
| GO:0007398~ectoderm development | 22 | 1.08E-05 |
| GO:0005925~focal adhesion | 15 | 1.45E-05 |
| GO:0008544~epidermis development | 20 | 3.82E-05 |

FIG. 3H

| Term | Count | P-value |
|---|---|---|
| GO:0006695~cholesterol biosynthetic process | 7 | 9.04E-06 |
| GO:0008202~steroid metabolic process | 16 | 1.10E-05 |
| GO:0006694~steroid biosynthetic process | 10 | 4.29E-05 |
| GO:0005768~endosome | 19 | 5.04E-05 |
| GO:0016126~sterol biosynthetic process | 7 | 5.49E-05 |
| GO:0008610~lipid biosynthetic process | 18 | 2.26E-04 |
| GO:0008203~cholesterol metabolic process | 9 | 4.50E-04 |
| GO:0016125~sterol metabolic process | 9 | 8.39E-04 |
| GO:0005783~endoplasmic reticulum | 34 | 1.14E-03 |

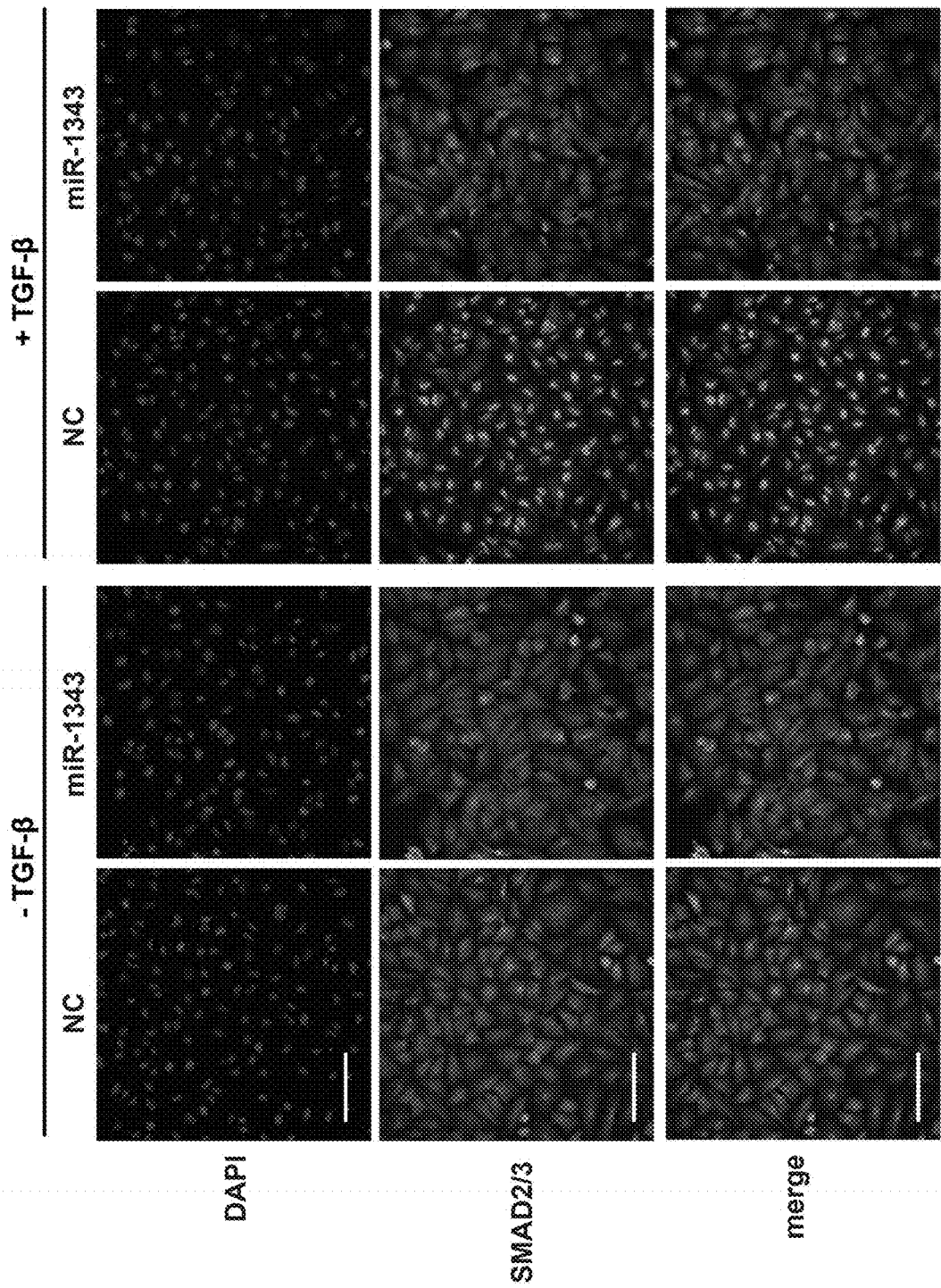

FIG. 7

TGFBR1 3'UTR

| | site 1 | site 2 | site 3 |
|---|---|---|---|
| | nt 147-153 | nt 164-171 | nt 214-220 |
| WT | CCCAGGA | CCCAGGA | CCCAGGA |
| MUT | CCGCGGA | CTTAAGA | CCGTCGA |

TGFBR2 3'UTR

| | site 1 |
|---|---|
| | nt 399-406 |
| WT | CCCAGGAA |
| MUT | CCGCGGAA |

ELMO2 3'UTR

| | site 1 | site 2 | site 3 | site 4 | site 5 |
|---|---|---|---|---|---|
| | nt 24-30 | nt 45-51 | nt 381-388 | nt 696-702 | nt 866-873 |
| WT | CCCAGGA | CCCAGGA | CCCAGGA | CCAGGAA | CCCAGGA |
| MUT | CTCGAGA | CCTAGTA | CCGCGGA | CCTAGGA | CCGCGGA |

MICRORNA TREATMENT OF FIBROSIS

CROSS REFERENCE TO RELATED APPLICATIONS

The present invention claims the priority benefit of U.S. Provisional Patent Application 62/204,782, filed Aug. 13, 2015, which is incorporated by reference in its entirety.

STATEMENT REGARDING FEDERAL FUNDING

This invention was made with government support under R01 HL117843 awarded by the National Institutes of Health. The government has certain rights in the invention.

FIELD

Provided herein are microRNAs that target transforming growth factor beta (TGF-β) receptors and attenuate pathways of fibrosis. In particular, microRNA-1343 reduces expression of TGFBR1 and TGFBR2, decreases TGF-β signaling, represses pathways of fibrosis, and treats fibrotic diseases.

BACKGROUND

Chronic diseases involving tissue fibrosis are a major health burden, resulting in irreversible damage to the fibrotic organ and the need for transplant. In most cases of fibrosis, disease progression involves repeated cycles of inflammation, followed by epithelial injury and repair, which in turn, causes scarring and tissue malfunction. The major molecule responsible for promoting tissue fibrosis is transforming growth factor beta (TGF-β), a cytokine normally released in response to injury that stimulates wound repair. However, overproduction of TGF-β can be damaging, and this phenomenon is consistently observed in fibrotic diseases, suggesting that TGF-β dysregulation can act as a driver of disease.

SUMMARY

Provided herein are microRNAs that target transforming growth factor beta (TGF-β) receptors and attenuate pathways of fibrosis. In particular, microRNA-1343 reduces expression of TGFBR1 and TGFBR2, decreases TGF-β signaling, represses pathways of fibrosis, and treats fibrotic diseases.

In some embodiments, provided herein are methods of treating or preventing fibrosis in a subject comprising administering a pharmaceutical composition comprising a miR-1343 molecule to the subject, wherein the miR-1343 molecule is miR-1343 (SEQ ID NO:43) or a functional variant thereof. In some embodiments, the functional variant comprises at least 70% (e.g., 70%, 75%, 80%, 85%, 90%, 95%, or more, or ranges therebetween) sequence identity with SEQ ID NO:43. In some embodiments, the functional variant comprises at least 70% (e.g., 70%, 75%, 80%, 85%, 90%, 95%, or more, or ranges therebetween) sequence similarity with SEQ ID NO: 43. In some embodiments, the miR-1343 molecule binds to a 3' untranslated region of TGFBR1 and/or TGFBR2. In some embodiments, the miR-1343 molecule inhibits expression of TGFBR1 and/or TGFBR2. In some embodiments, the subject suffers from a pulmonary form of fibrosis. In some embodiments, the subject suffers from idiopathic pulmonary fibrosis, chronic obstructive pulmonary disease, and/or cystic fibrosis.

In some embodiments, the miR-1343 molecule is vesicle formulated. In some embodiments, the miR-1343 molecule is administered by inhalation, topically, transdermally, or by injection. In some embodiments, the miR-1343 molecule is administered to epithelial cells of the subject. In some embodiments, the miR-1343 molecule is administered directly to the epithelial cells. In some embodiments, the miR-1343 molecule is administered systemically and localizes in the epithelial cells. In some embodiments, the miR-1343 molecule is administered to pulmonary epithelial cells.

In some embodiments, provided herein are methods of treating or preventing fibrosis in a subject comprising enhancing production of miR-1343 in the subject. In some embodiments, the subject suffers from a pulmonary form of fibrosis. In some embodiments, the subject suffers from idiopathic pulmonary fibrosis, chronic obstructive pulmonary disease, and/or cystic fibrosis. In some embodiments, the production of miR-1343 is enhanced in pulmonary epithelial cells of a subject. In some embodiments, enhancing production of miR-1343 in the subject comprises administering a miR-1343 enhancing agent to the subject or epithelial cells of the subject. In some embodiments, the miR-1343 enhancing agent interacts with the cellular machinery to increase production of miR-1343 within the subject or epithelial cells of the subject. In some embodiments, the miR-1343 enhancing agent is a nucleic acid. In some embodiments, the nucleic acid encodes a miR-1343 molecule or sequences to facilitate miR-1343 production within the subject. In some embodiments, the nucleic acid inhibits expression of an inhibitor of miR-1343 production or activity by antisense or RNA interference. In some embodiments, the nucleic acid alters the genomic DNA of the cells of the subject to enhance the subject's own miR-1343 production.

In some embodiments, provided herein are pharmaceutical compositions comprising a miR-1343 molecule and a pharmaceutically-acceptable carrier. In some embodiments, the miR-1343 molecule is miR-1343 (SEQ ID NO:43) or a functional variant thereof. In some embodiments, the functional variant comprises at least 70% (e.g., 70%, 75%, 80%, 85%, 90%, 95%, or more, or ranges therebetween) sequence identity with SEQ ID NO:43. In some embodiments, the functional variant comprises at least 70% (e.g., 70%, 75%, 80%, 85%, 90%, 95%, or more, or ranges therebetween) sequence similarity with SEQ ID NO:43. In some embodiments, the miR-1343 molecule is vesicle formulated. In some embodiments, the miR-1343 molecule binds to a 3' untranslated region of TGFBR1 and/or TGFBR2. In some embodiments, the miR-1343 molecule inhibits expression of TGFBR1 and/or TGFBR2.

BRIEF DESCRIPTION OF THE DRAWINGS

FIGS. 2A-C: miR-1343 targets the 3' UTRs of TGFBR1, TGFBR2, and ELMO2.) A) TargetScan analysis of miR-1343 predicted target genes. More negative context scores are most significant. (B) Luciferase assay of A549 cells transiently transfected with either wild type (WT) or mutant (MUT) pMIR-REPORT-3' UTR constructs along with miR-1343 or negative control (NC) miRNA. Luciferase values were normalized to pMIR-β-galactosidase levels and illustrated relative to the NC.  p≤0.01, ** p≤0.0001, ns=not significant. (C) Luciferase assay of A549 cells transiently transfected with WT pMIR-REPORT-TGFBR1 3' UTR or MUT constructs in which various seed sites were mutated along with miR-1343 or NC miRNA. Bars to the left illustrate the TGFBR1 3' UTR with miR-1343 seed sites 1, 2, and 3. Site 1 and 3 are conserved while site 2 is non-conserved. "X" denotes miR-1343 seed sites that were mutated, which are shown in FIG. 7. Luciferase values were normalized to pMIR-β-galactosidase levels and illustrated relative to the NC. p values as for (b).

FIGS. 3A-H: The impact of miR-1343 on gene expression in 16HBE14o- and A549 cells; RNA-seq identifies multiple pathways relevant to airway disease and fibrosis. (A) Heatmaps illustrating relative expression of differentially expressed genes (DEGs) following miR-1343 or negative control (NC) miRNA transient expression in 16HBE14o- or A549 cells. Each line represents a different gene. (B) Venn diagram of DEGs identified by RNA-seq in A549 versus 16HBE14o-cells. Overlapping region represents the number of DEGs identified in both cell types. (C) Gene expression levels measured by RT-qPCR assays following 48 hours of miR-1343 or NC miRNA transient transfection in A549 cells. RT-qPCR Ct values were normalized to beta-2-microglobulin ((32M). * p≤0.05,  p≤0.01, * p≤0.001, **** p≤0.0001, ns=not significant. (D) Gene expression levels measured by RT-qPCR assays following 48 hours of miR-1343 or NC miRNA transient transfection in primary lung fibroblasts. RT-qPCR Ct values were normalized to β2M. p-values as for (c). (E) Western blots of A549 lysates transfected with miR-1343 or NC miRNA for 48 hours and probed with antibodies specific to TGFBR1, TGFBR2 and ELMO2. GAPDH was the loading control. (F) Western blots of lysates from primary lung fibroblasts transfected with miR-1343 or NC miRNA for 48 hours and probed with antibodies specific to TGFBR1, TGFBR2 and ELMO2. GAPDH was the loading control. (G-H) DAVID gene ontology analysis of down-regulated (G) or up-regulated (H) genes identified by RNA-seq in both A549 and 16HBE14o- cells following miR-1343 or NC miRNA transient expression.

FIGS. 4A-C: Overexpression of miR-1343 reduces canonical TGF-β signaling. (A) Luciferase assay of A549 cells transiently transfected with the p3TP-lux vector and either miR-1343 or negative control (NC) miRNA. Forty-eight hours post-transfection, cells were treated with TGF-β$_1$ (5 ng/mL) or vehicle control (0 ng/mL) for 24 hours. Luciferase values were normalized to pMIR-β-galactosidase levels and expressed relative to NC treated with vehicle. **** p≤0.0001. (B) miR-1343 represses phosphorylation of SMAD2/3. Western blot of lysates from A549 cells transiently transfected with miR-1343 or NC miRNA and treated with TGF-β$_1$ (5 ng/mL, +) or vehicle control (-) for the indicated period of time. Blots were probed with antibodies specific for pSMAD2, phorphorylated (active) SMAD2; pSMAD3, phosphorylated (active) SMAD3; total SMAD2/3, top band represents SMAD2 and bottom band represents SMAD3. GAPDH was the loading control. (C) miR-1343 inhibits nuclear localization of pSMAD2/3. Representative images of immunofluorescence in A549 cells transiently transfected with miR-1343 or NC miRNA and treated with TGF-β$_1$ (50 ng/mL, +) or vehicle control (-) for 1 hour. Fluorescence shows total SMAD2/3 and DAPI is the nuclear counterstain. Merge illustrates total SMAD2/3 plus DAPI. Scale bar=100 µm.

FIG. 7: Seed sites for miR-1343 within the TGFBR1, TGFBR2, and ELMO2 3' UTRs. WT, wild type; MUT, mutant. Underlined nucleotides denote mutated bases.

DEFINITIONS

Figures 1A, 1B:
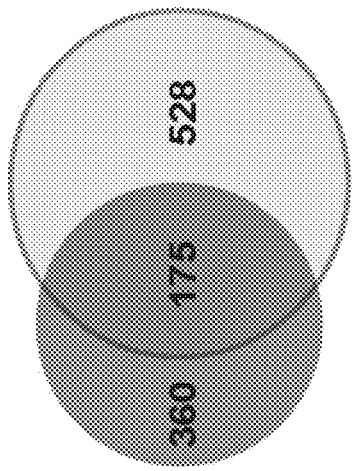
FIGS. 1A-C: miR-1343 is the most significant microRNA predicted to target the TGF-β receptors. (A) Venn diagram illustrating the number of TargetScan-predicted miRNAs to target the TGFBR1 and TGFBR2 3' UTRs. Overlapping region depicts miRNAs that are predicted to target both receptors. (B) Top miRNAs that are predicted to target both TGFBR1 and TGFBR2. Context scores are generated from TargetScan, with the more negative context scores being the most significant. (C) miR-1343 location at the chromosome 11p13 CF modifier locus and organization of its stem-loop structure.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions (e.g., definitions listed below of contained throughout the detailed description), will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a miR-1343 oligonucleotide" is a reference to one or more miR-1343 oligonucleotides, unless the context clearly dictates otherwise.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "fibrosis" refers to the formation or development of excess fibrous connective tissue, such as collagen, in an organ or tissue, typically as part of a reparative process of disease state, as opposed to a formation of healthy amounts of fibrous tissue (e.g., collagen) as a normal constituent of an organ or tissue. Fibrosis may occur in the lung (e.g., pulmonary fibrosis), heart, kidney, muscle, skin, soft tissue (e.g. mediastinum or retroperitoneum), joint (e.g. knee, shoulder or other joints), etc. In particular, the term "fibrosis" includes, pulmonary fibrosis, idiopathic pulmonary fibrosis, chronic obstructive pulmonary disease, cystic fibrosis, cirrhosis endomyocardial fibrosis, mediastinal fibrosis, myelofibrosis, retroperitoneal fibrosis, progressive massive fibrosis (a complication of coal workers' pneumoconiosis), nephrogenic systemic fibrosis, renal fibrosis, Crohn's disease, keloid, hypertrophic scarring, old myocardial infarction, scleroderma/systemic sclerosis, arthrofibrosis and some forms of adhesive capsulitis.

As used herein, the term "physiologic conditions" refers to solution or reaction conditions roughly simulating those most commonly found in mammalian organisms, particularly humans (e.g., not relating to specific microenvironments within organisms (e.g., not the acidic conditions (pH 5.0) commonly found in tumor microenvironments and cellular late endosomes) or other rare conditions, unless specifically-noted). While variables such as temperature, availability of cations, and pH ranges may vary, "physiologic conditions" typically mean a temperature of 35-40° C., with about 37° C. being particularly preferred, and a pH of 7.0-8.0, with about 7.5 being particularly preferred. The conditions may also include the availability of cations, preferably divalent and/or monovalent cations, with a concentration of about 2-15 mM $Mg^{2+}$ and 0 1.0 M $Na^+$ being particularly preferred.

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a subject that is being treated for a disease or condition (e.g., fibrosis).

As used herein, the term "sample" refers to any material, biological fluid, tissue, or cell obtained or otherwise derived from a subject. This includes blood (e.g., whole blood, leukocytes, peripheral blood mononuclear cells, buffy coat, plasma, and serum), sputum, tears, mucus, nasal washes, nasal aspirate, breath, urine, semen, saliva, peritoneal washings, ascites, cystic fluid, meningeal fluid, amniotic fluid, glandular fluid, lymph fluid, nipple aspirate, bronchial aspirate, bronchial brushing, synovial fluid, joint aspirate, organ secretions, cells, a cellular extract, and cerebrospinal fluid. This also includes experimentally separated fractions of all of the preceding. For example, a blood sample can be fractionated into serum, plasma, or into fractions containing particular types of blood cells, such as red blood cells or white blood cells (leukocytes). In some embodiments, a sample can be a combination of samples from an individual, such as a combination of a tissue and fluid sample. The term "sample" may also include materials containing homogenized solid material, such as from a stool sample, a tissue sample, or a tissue biopsy; and materials derived from a tissue culture or a cell culture. Any suitable methods for obtaining a sample can be employed; exemplary methods include, e.g., phlebotomy, swab, and a fine needle aspirate biopsy procedure. Exemplary tissues susceptible to fine needle aspiration include lymph node, lung, lung washes, BAL (bronchioalveolar lavage), thyroid, breast, pancreas, and liver. Samples can also be collected, e.g., by micro dissection, bladder wash, smear, or ductal lavage. A sample obtained or derived from an individual includes any such sample that has been processed in any suitable manner (e.g., filtered, diluted, pooled, fractionated, concentrated, etc.) after being obtained from the individual.

The term "effective dose" or "effective amount" refers to an amount of an agent that results in the reduction of symptoms in a patient or results in a desired biological outcome. In certain embodiments, an effective dose or effective amount is sufficient to treat or reduce symptoms of a disease or condition (e.g., fibrosis).

As used herein, the terms "administration" and "administering" refer to the act of giving a drug, prodrug, or other agent, or therapeutic to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

The term "treatment" encompasses both therapeutic and prophylactic/preventative measures unless otherwise indicated. Those in need of treatment include, but are not limited to, individuals already having a particular condition as well as individuals who are at risk of acquiring a particular condition or disorder (e.g., those having a genetic or epigenetic predisposition; based on age, gender, lifestyle, etc.). The term "treating" refers to administering an agent to a subject for therapeutic and/or prophylactic/preventative purposes.

As used herein, the terms "co-administration" and "co-administering" refer to the administration of at least two agent(s) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

DETAILED DESCRIPTION

Provided herein are microRNAs that target transforming growth factor beta (TGF-β) receptors and attenuate pathways of fibrosis. In particular, microRNA-1343 reduces expression of TGFBR1 and TGFBR2, decreases TGF-β signaling, represses pathways of fibrosis, and treats fibrotic diseases.

Experiments conducted during development of embodiments of the present invention demonstrate that microRNA-1343 (miR-1343) significantly reduces the expression of both of the canonical TGF-β receptors, TGFBR1 and TGFBR2, which leads to substantial decreases in TGF-β signaling and corresponding fibrotic phenotypes. In particular, experiments demonstrate miR-1343 regulation of lung fibrosis phenotypes associated with TGF-β signaling in multiple contributing respiratory cell types. However, in some embodiments, miR-1343 treatment is applicable to any fibrotic disease due to similarities in TGF-β signaling and disease progression. miR-1343 was identified as being the most significant microRNA to target both TGF-β receptor genes, the initiating proteins of the TGF-β signaling pathway. Luciferase assays confirmed miR-1343 to directly repress TGF-β receptor 1 and receptor 2 expression via their 3' untranslated regions. Furthermore, RNA-sequencing and in vitro gene expression assays validated miR-1343 to control endogenous TGF-β receptor 1 and 2 expression in lung epithelial cells and fibroblasts. It was also verified that several other genes to be directly down-regulated by miR-1343, and hundreds more involved in lung function to be impacted by miR-1343 overexpression, either directly or indirectly. As a result of its receptor targeting, miR-1343 was found to significantly repress canonical TGF-β signaling by reducing levels of phosphorylated SMAD2 and SMAD3 and preventing their translocation to the nucleus. Fibrotic markers, such as αSMA and COL1A1, were reduced in the presence of miR-1343, while negative markers of epithelial-to-mesenchymal transition were increased. It was demonstrated that miR-1343 most highly expressed in cells of myeloid origin and epithelial cells under conditions of stress. Results demonstrate the functionality of miR-1343 in repressing TGF-β signaling, and indicate an important role for this microRNA in protecting against fibrosis in many different diseases.

The lung epithelium serves as a regulator of respiratory health. Not only does the epithelium perform a barrier function, protecting the pulmonary interstitium from harmful pathogens and environmental particles, but it also serves as an important site for host defense, mucociliary clearance, and gas exchange (ref 1; herein incorporated by reference in its entirety). Disruption of epithelial integrity underlies several chronic lung diseases, including cystic fibrosis (CF), idiopathic pulmonary fibrosis (IPF), and chronic obstructive pulmonary disease (COPD). In these disorders, a significant proportion of epithelial dysfunction results from lung fibrosis and architectural tissue remodeling. These processes gradually replace healthy, elastic lung epithelium with fibrous connective tissue, composed mainly of collagens and extracellular matrix (ECM) components. The pathways of fibrosis impede normal epithelial function and directly lead to lung obstruction (ref.2; herein incorporated by reference in its entirety).

Transforming growth factor beta (TGF-β) has a pivotal role in initiating mechanisms of tissue fibrosis. This cytokine is normally released in response to injury and stimulates cell differentiation and wound healing (ref.3; herein incorporated by reference in its entirety). High levels of TGF-β are consistently observed in fibrotic lung diseases, in turn promoting excessive repair processes leading to organ dysfunction (refs. 4-7; herein incorporated by reference in their entireties). TGF-β attracts and induces the differentiation of resident or circulating fibroblasts into contractile myofibroblasts in the lung, which migrate to sites of injury and produce ECM (ref 3; herein incorporated by reference in its entirety). Furthermore, TGF-β promotes epithelial-to-mesenchymal transition (EMT), a process whereby alveolar epithelial cells in the lung can transdifferentiate into migratory fibroblastic cells (ref.8; herein incorporated by reference in its entirety).

The initiating events for each fibrotic lung disease are distinct; however, an absence of correlation between the primary insult and disease severity is a common feature. This implies possible genetic contributions that modify disease development and/or progression (refs. 9-11; herein incorporated by reference in their entireties). Universally, TGF-β is implicated as a major factor underlying fibrotic phenotypes, and polymorphisms promoting increased TGF-β expression were identified as genetic modifiers of COPD and CF lung disease severity (refs. 12-15; herein incorporated by reference in their entireties).

MicroRNAs (miRNAs) are small 21-25 nucleotide noncoding RNAs that repress genes post-transcriptionally. Panels of misregulated miRNAs have been observed in a variety of human diseases, including pulmonary fibrosis (refs. 16-18; herein incorporated by reference in their entireties). miR-155 exhibited pro-fibrotic and pro-inflammatory roles in models of both IPF and CF, in which it regulated expression of keratinocyte growth factor and interleukin-8 (refs. 19,20; herein incorporated by reference in their entireties). Furthermore, IPF and CF patient respiratory tissues showed up-regulation of miR-21 and miR-145 expression, respectively, and both miRNAs activated pulmonary fibroblasts and exacerbated experimental fibrosis in mice (refs. 21-23; herein incorporated by reference in their entireties). Conversely, overexpression of miR-29 and miR-31 inhibited markers of fibrosis in mouse models and normal lung fibroblasts, demonstrating protective roles (refs. 24-26; herein incorporated by reference in their entireties).

Experiments were conducted during development of embodiments of the present invention demonstrating the role of miR-1343 in attenuating TGF-β signaling and pathways of fibrosis in primary fibroblasts and lung epithelial cell lines. miR-1343 was identified in several small RNA-sequencing studies in humans, cows, and pigs (refs. 27-31; herein incorporated by reference in their entireties). miR-1343 was identified using in silico tools to predict miRNAs targeting the 3' untranslated (3' UTR) regions of both TGF-β receptor genes, which would in turn inhibit TGF-β signaling. The genomic location of miR-1343 adjacent to a modifier locus for CF lung disease severity (ref.32; herein incorporated by reference in its entirety) made it a compelling miRNA for further investigation. Data show that miR-1343 represses TGF-β signaling as well as TGF-β-induced fibrotic markers and EMT.

In contrast to several previous reports that identified miRNAs involved in pathways of fibrosis through comparisons of normal and fibrotic tissue (refs. 18,20-22; incorporated by reference in their entireties), or by differential gene expression in primary cells and cancer cell lines (ref. 16; incorporated by reference in its entirety), miR-1343 was identified by searching for miRNAs that directly target the TGF-β receptors.

It was demonstrated that miR-1343 binds to seed sites in the 3'UTR of TGFBR1 and TGFBR2 and represses endogenous levels of the receptors. In turn, miR-1343 represses canonical TGF-β-signaling pathways in several cell types as shown by inhibition of SMAD2/3 phosphorylation and nuclear translocation. Subsequent to TGF-β exposure, miR-1343 also reduces expression of markers of fibrosis, such as αSMA and COL1A1.

The genomic location of miR-1343 is in a region marked by single nucleotide polymorphisms (SNPs) that associate with lung disease severity in F508del CF (ref 32; herein incorporated by reference in its entirety). The GWAS implicated 4 genes that are close to the critical interval at chromosome 11p13, of which two (Ets homologous factor (EHF) and E74-like factor 5 (ELF5)) are epithelial-specific transcription factors and two (APAF interacting protein (APIP) and Pyruvate dehydrogenase complex component X (PDHX)) are ubiquitously expressed genes involved in basic cellular processes. It was demonstrated that EHF regulates genes important for maintenance of the lung epithelial barrier and its response to injury (ref 42; herein incorporated by reference in its entirety). Since miR-1343 is located within an intron of the PDHX gene, which is involved in the conversion of pyruvate to acetyl coenzyme A in mitochondrial metabolism, expression of these two genes may be co-regulated.

Neutrophils, the most abundant myeloid cells in humans, are key regulators of respiratory function and are among the first cells recruited to sites of injury where they work to clear infection and amplify the inflammatory response (ref.44; herein incorporated by reference in its entirety). Sustained neutrophil influx, survival, and activation are all processes regulated by TGF-β signaling and are known to enhance lung fibrosis (ref.45; herein incorporated by reference in its entirety). Data showing miR-1343 to target TGFBR1 and TGFBR2 to reduce TGF-β signaling indicates that miR-1343 in neutrophils interferes with the pathways to block fibrosis. Several studies showed that HL-60 cells and other myeloid cell types secrete exosomes containing a variety of RNA molecules, including miRNAs (refs. 46,47; herein incorporated by reference in their entireties). These exosomes can be taken up by other cells, for example in the bone marrow, where they alter gene expression (ref.47; herein incorporated by reference in its entirety).

The observation that miR-1343 processing is induced by stress in A549 cells indicates that this miRNA also regulates response to injury in lung epithelial cells. Serum starvation is a known stress inducer in cultured cells (ref.48; herein incorporated by reference in its entirety). miRNA expression is known to be induced by various forms of cell stress (refs. 49-51; herein incorporated by reference in their entireties), and activity of miRNAs can also be modulated following amino acid starvation (ref.52; herein incorporated by reference in its entirety) or hippuristanol-induced stress (ref.53; herein incorporated by reference in its entirety).

Embodiments described herein may be used to reduce TGF-β signaling in vitro or in vivo, and find use in the treatment of fibroproliferative diseases including, but not limited to, lung fibroses, liver cirrhosis, cardiovascular disease, systemic sclerosis, kidney disease, and autoimmune diseases. miR-1343 specifically targets the proteins that initiate TGF-β signaling to repress fibrosis (rather than targeting downstream TGF-β signaling targets), is applicable to the treatment of all types of TGF-β-induced fibrosis in many organ types, and targets the source of fibrosis to alleviate disease progression, rather than symptomatic treatment which is the current standard of care.

In some embodiments, miR-1343 molecules are administered to a subject to treat or prevent fibrosis or related conditions. miR-1343 molecules include "substantially identical" sequences, for example, sequences that are substantially identical to the natural miR-1343 sequence (e.g., SEQ ID NO: 43) described herein. A "substantially identical" sequence as used herein is a nucleotide sequence that differs from a miR-1343 sequence or the complement thereof only by one or more substitutions located at positions of the sequence that do not destroy the biological function of the nucleic acid molecule. By "biological function" is meant promoting inhibiting expression of TGFR1 and/or TGFR2, and/or inhibiting TGF-β signaling and/or TGF-β signaling. A substantially identical sequence can be any integer from 60% to 99%, or more generally at least 60%, or at least 65%, 75%, 80%, 85%, 90%, or 95%, or as much as 96%, 97%, 98%, or 99% identical when optimally aligned at the nucleotide level to the miR-1343 sequence. The length of comparison sequences may be at least 5, 6, 7, 8, 9, 10, 11, 12, 13, 14, 15, 16, 17, 18, 19, 20, 21, 22, 23, 24 or 25 nucleotides, or at least 30, 35, 40, 45, or 50 nucleotides, or any integer value therebetween. In alternate embodiments, the length of comparison sequences may be at least 55, 60, 65, 70, 75, 80, 85, 90, 95, 100, 105, 110, 115 or 120 nucleotides, or any integer value therebetween.

Alternatively, or additionally, two nucleic acid sequences may be "substantially identical" if they hybridize under high stringency conditions that allow hybridization between homologous sequences, but do not allow substantial hybridization of non-homologous sequences. In some embodiments, high stringency conditions are, for example, conditions that allow hybridization at 0.02-0.15M NaCl at temperatures of about 30° C. to about 70° C., or about 40° C. to about 60° C. Exemplary stringent hybridization conditions include 50% formamide, 5×SSC, 1% SDS at 42° C., or 5×SSC, 1% SDS at 65° C. Hybridizations may be carried out over a period of about 20 to 30 minutes, or about 2 to 6 hours, or about 10 to 15 hours, or over 24 hours or more. A common technique for hybridization of RNA molecules in Northern hybridization. The high stringency conditions used in such techniques are well known to those skilled in the art of molecular biology, and examples of them can be found, for example, in Ausubel et al., Current Protocols in Molecular Biology, John Wiley & Sons, New York, N.Y., 1998, which is hereby incorporated by reference. It is to be understood that stringency conditions, including conditions of high stringency, vary according to the probe/primer and target sequences and that a person of ordinary skill in the art is readily able to determine such conditions using routine techniques. In some embodiments, substantially identical sequences include sequences that hybridize under high stringency conditions to miR-1343 or to a complement thereof.

In some embodiments, miR-1343 molecules include, without limitation, the miR-1343 molecules described herein and fragments and variants and modifications thereof, for example, those that have an improved property e.g., biological or physiochemical or pharmaceutical properties. An "improved" property includes, without limitation, enhanced inhibition of expression of TGFR1 and/or TGFR2, and/or inhibiting TGF-β signaling and/or TGF-β signaling.

A "fragment" of a miR-1343 molecule may be about 5, 6, 7, 8, 9, 10, 11, 12, 13, 14, 15, 16, 17, 18, 19, 20, 21, 22, 23, 24 or 25 nucleotides, or at least 30, 35, 40, 45, or 50 nucleotides, or at least 55, 60, 65, 70, 75, 80, 85, 90, 95, 100, 105, 110, 115 or 120 nucleotides in length, or any integer value therebetween. A fragment of a miR-1343 precursor molecule may include a corresponding mature or star sequence. A "variant" miR-1343 molecule includes a molecule that has less than 100% nucleotide identity to a wild type miR-1343 molecule (e.g., SEQ ID NO: 43)) as exemplified herein or known in the art. A "variant" miR-1343 molecule also includes miR-1343 molecules from different species, or miR-1343 molecules containing one or more nucleotide substitutions, deletions or insertions. In some embodiments, a miR-1343 molecule may be nuclease resistant by for example incorporation of a ribonucleotide modified into the 2'-position. Exemplary 2'-modified ribonucleotides include those modified at the 2' position with fluoro, amino, alkyl, alkoxy, and O-allyl.

In some embodiments, "variant" miR-1343 molecule also includes miR-1343 molecules having modifications including, but are not limited to, replacement of the phosphate groups/phosphodiester linkages on the oligonucleotide backbone, replacement of phosphate and/or hydroxyl groups on the nucleotide at the 5'-terminus of the oligonucleotide or modifications of the sugar (ribose) moieties with various groups including but not limited to 2 O-Me substitutions. One example of a variant RNA is phosphorothioate RNA.

In some embodiments, a variant of miR-1343 is administered (e.g., a functional variant). In some embodiments, a variant of miR-1343 has at least 50% (e.g., 50%, 60%, 70%, 80%, 90%, 95%, 98%, 99%, etc.) sequence identity or sequence similarity with miR-1343 (SEQ ID NO:1). In some embodiments, a variant miR-1343 molecule comprises 1 or more substitutions (e.g., 1, 2, 3, 4, 5, 6, 7, 8, 9, 10, or more, or ranges therebetween) relative to a natural miR-1343 sequence (e.g., SEQ ID NO: 43). In some embodiments, a variant miR-1343 molecule comprises 1 or more conservative substitutions (e.g., 1, 2, 3, 4, 5, 6, 7, 8, 9, 10, or more, or ranges therebetween) relative to a natural miR-1343 sequence (e.g., SEQ ID NO: 43). In some embodiments, a variant miR-1343 molecule comprises 1 or more non-conservative substitutions (e.g., 1, 2, 3, 4, 5, 6, 7, 8, 9, 10, or more, or ranges therebetween) relative to a natural miR-1343 sequence (e.g., SEQ ID NO: 43).

As used herein, the term "percent sequence identity" refers to the degree (e.g., 50%, 60%, 70%, 80%, 90%, 95%, 98%, 99%, etc.) to which two polymer sequences (e.g., peptide, polypeptide, nucleic acid, etc.) have the same sequential composition of monomer subunits. If two polymers have identical sequences (e.g., 100% sequence identity) they may be referred to herein as having "sequence identity." The term "percent sequence similarity" refers to the degree (e.g., 50%, 60%, 70%, 80%, 90%, 95%, 98%, 99%, etc.) with which two polymer sequences (e.g., peptide, polypeptide, nucleic acid, etc.) have similar polymer sequences. For example, similar amino acids are those that share the same biophysical characteristics and can be grouped into the families (see above). If two polymers have sequences that have monomers at each position that share the same biophysical characteristics they may be referred to herein as having "sequence similarity." The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

A "conservative" amino acid substitution refers to the substitution of an amino acid in a polypeptide with another amino acid having similar properties, such as size or charge. In certain embodiments, a polypeptide comprising a conservative amino acid substitution maintains at least one activity of the unsubstituted polypeptide. A conservative amino acid substitution may encompass non-naturally occurring amino acid residues, which are typically incorporated by chemical peptide synthesis rather than by synthesis in biological systems. These include, but are not limited to, peptidomimetics and other reversed or inverted forms of amino acid moieties. Naturally occurring residues may be divided into classes based on common side chain properties, for example: hydrophobic: norleucine, Met, Ala, Val, Leu, and Ile; neutral hydrophilic: Cys, Ser, Thr, Asn, and Gln; acidic: Asp and Glu; basic: His, Lys, and Arg; residues that influence chain orientation: Gly and Pro; and aromatic: Trp, Tyr, and Phe. Non-conservative substitutions may involve the exchange of a member of one of these classes for a member from another class; whereas conservative substitutions may involve the exchange of a member of one of these classes for another member of that same class.

A miR-1343 molecule is "substantially pure" or "isolated" when it is separated from the components that naturally accompany it. Typically, a miR-1343 molecule is substantially pure when it is at least 10%, 20%, 30%, 40%, 50%, or 60%, more generally 70%, 75%, 80%, or 85%, or over 90%, 95%, or 99% by weight, of the total material in a sample. Thus, for example, a miR-1343 molecule that is chemically synthesized, produced by recombinant technology, or isolated by known purification techniques, will be generally be substantially free from its naturally associated components. A substantially pure miR-1343 molecule therefore can be obtained, for example, by extraction from a natural source; by expression of a recombinant nucleic acid molecule encoding the miR-1343 molecule; or by chemical synthesis.

Embodiments herein are not limited by the route of administration. In some embodiments, the appropriate route of administration is selected based upon the type of fibrosis, the underlying cause, the location of the fibrosis, etc. Suitable routes of administration include, but are not limited to, oral, intravenous, rectal, aerosol, parenteral, ophthalmic, pulmonary, transmucosal, transdermal, vaginal, optic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In some embodiments, a miR-1343 molecule is formulated for oral administration, for example, by combining the active agent with, e.g., pharmaceutically acceptable carriers or excipients. In various embodiments, a miR-1343 molecule is formulated in oral dosage forms that include, by way of example only, tablets, powders, pills, dragees, capsules, liquids, gels, syrups, elixirs, slurries, suspensions and the like.

In other embodiments, a miR-1343 molecule is administered topically. Topical administration may be particularly useful for treatment or prevention of scarring resulting from injury or surgery. The miR-1343 molecule may be formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In some embodiments, a miR-1343 molecule is formulated for transdermal administration. Transdermal formulations may employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of a miR-1343 molecule is accomplished by means of iontophoretic patches and the like. In certain embodiments, transdermal patches provide controlled delivery of a miR-1343 molecule. In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing a a miR-1343 molecule optionally with carriers, optionally a rate controlling barrier to deliver the compound to the skin of the host at a controlled and predetermined rate over a prolonged period of time, and means to secure the device to the skin.

In other embodiments, a miR-1343 molecule is formulated for administration by inhalation. Such delivery may be particularly useful for the treatment and/or prevention of pulmonary forms of fibrosis (e.g., idiopathic pulmonary fibrosis). Various forms suitable for administration by inhalation include, but are not limited to, aerosols, mists or powders. miR-1343 molecules are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator are formulated containing a powder mix of a miR-1343 molecule and a suitable powder base such as lactose or starch.

As addressed above, other routes of administration, useful for the treatment of particular conditions or delivery to particular cells, tissues, organs, etc. are contemplated.

In some embodiments, miR-1343 molecules are co-administered with other treatments/therapies for fibrosis. For example, for pulmonary fibrosis, in some embodiments, a miR-1343 molecule is co-administered (e.g., sequentially or simultaneously) with one or more of corticosteroids (e.g., prednisone), cyclophosphamide, azathioprine, Mycophenolate mofetil, N-acetylcysteine, Nintedanib, Pirfenidone, Proton pump inhibitors, Supplemental Oxygen Therapy, etc. For other forms of fibrosis, other appropriate therapeutics may be co-administered for the treatment of the fibrosis or an underlying or related condition.

In some embodiments, a miR-1343 molecule may be effectively delivered to cells or tissues by a variety of methods known to those skilled in the art. Such methods include but are not limited to liposomal encapsulation/delivery, vector-based gene transfer, fusion to peptide or immunoglobulin sequences for enhanced cell targeting and other techniques. Suitable viral vectors include retroviral vectors such as lentiviral vectors, adenovirus vectors, adeno-associated virus vectors, etc. In some embodiments, a miR-1343 molecule, may also be formulated in pharmaceutical compositions well known to those in the field. These include liposomal formulations and combinations with other agents or vehicles/excipients such as cyclodextrins which may enhance delivery of the miRNA. In some embodiments, suitable carriers include lipid-based carriers such as a stabilized nucleic acid-lipid particle (e.g., SNALP or SPLP), cationic lipid or liposome nucleic acid complexes (i.e., lipoplexes), a liposome, a micelle, a virosome, or a mixture thereof. In other embodiments, the carrier system is a polymer-based carrier system such as a cationic polymer-nucleic acid complex (i.e., polyplex). In some embodiments, the carrier system is a cyclodextrin-based carrier system such as a cyclodextrin polymer-nucleic acid complex. In further embodiments, the carrier system is a protein-based carrier system such as a cationic peptide-nucleic acid complex.

Experiments conducted during development of embodiments herein demonstrate that miR-1343 is delivered to epithelial cells (e.g., pulmonary epithelial cells) by exosomes. In some embodiments, miR-1343 molecules are formulated for therapeutic administration in a exosome or exosome-like carrier. In some embodiments, a carrier is a vesicle with a diameter of about 10 nm to 200 nm (e.g., 10 nm, 20 nm, 30 nm, 40 nm, 50 nm, 60 nm, 70 nm, 80 nm, 90 nm, 100 nm, 125 nm, 150 nm, 175 nm, 200 nm, and ranges therebetween). In some embodiments, a carrier is a natural or synthetic membrane-bound vesicle.

Suitable carriers are known in the art and are described in, without limitation, United States Patent Application Nos. 20070173476 published Jul. 26, 2007; 20050008617 published Jan. 13, 2005; 20050014962 published Jan. 20, 2005; 20050064595 published Mar. 24, 2005; 20060008910 published Jan. 12, 2006; 20060051405 published Mar. 9, 2006; 20060083780 published Apr. 20, 2006; 20050008689 published Jan. 13, 2005; 20070172950 published Jul. 26, 2007; U.S. Pat. No. 7,101,995 issued Sep. 5, 2006 to Lewis, et al.; U.S. Pat. No. 7,220,400 issued May 22, 2007, to Monahan, et al.; U.S. Pat. No. 5,705,385 issued Jan. 6, 1998 to Bally, et al.; U.S. Pat. No. 5,965,542 issued Oct. 12, 1999 to Wasan, et al.; U.S. Pat. No. 6,287,591 issued Sep. 11, 2001 to Semple, et al., all of which are hereby incorporated by reference.

EXPERIMENTAL

Example 1

Materials and Methods

Cell Culture

A549 lung adenocarcinoma cells (ref 62; herein incorporated by reference in its entirety), 16HBE14o-SV40 ori-transformed human bronchial epithelial cells (ref 63; herein incorporated by reference in its entirety), and Caco2 colorectal adenocarcinoma cells (ref.64; herein incorporated by reference in its entirety) were cultured in Dulbecco's Modified Eagle Medium (DMEM, low glucose) supplemented with 10% fetal bovine serum (FBS). Primary lung fibroblasts were cultured in DMEM (high glucose) supplemented with 10% FBS and 1× Penicillin/Streptomycin for ≤7 passages.

Cloning and Mutagenesis

3' UTRs were amplified from human genomic DNA according to TargetScan and UCSC gene annotations using Phusion Polymerase (NEB). Mutagenesis of seed sites was performed using the QuikChange Lightning Site-Directed Mutagenesis Kit (Agilent). See Table 1a for cloning primers and Supplementary Table 1b for mutagenesis primers that were used.

TABLE 1

Primers used for (a) cloning of 3' UTRs, (b) mutagenesis of miR-1343 seed sequences within cloned 3' UTRs, and (c) SYBR Green qPCR assays.

a.

| Cloned Region | Primers | SEQ ID NO: |
|---|---|---|
| TGFBR1 3' UTR | F: 5'-GGACTAGTTTCTACAGCTTTGCCTGAA CTCTC | 1 |
| | R: 5'-CGACGCGTCCTTCGCCTTCCTAGAAAAA | 2 |
| TGFBR2 3' UTR | F: 5'-CTGCCCCTGAACTGATGCTT | 3 |
| | R: 5'-GGTCCAGGTAGGCAGTGGAA | 4 |
| ELMO2 3' UTR | F: 5'-CCTGGAGCCAGAAACGAC | 5 |
| | R: 5'-CATGGTTACTGACAGGAAGC | 6 |
| SMAD2 3' UTR | F1: 5'-ACTAGTGCATTGATACTGCTGGCACC | 7 |
| | R1: 5'-GAGCTCGCACAAAGTCTGGAAGCAAGC | 8 |
| | F2: 5'-ACTAGTTCTGTTGCCCAACCTGGAG | 9 |
| | R2: 5'-GAGCTCGAGATCACCTGTGGGTCAAGG | 10 |
| SMURF1 3' UTR | F1: 5'-CCTAGGGCAACCAAAGGCAACAGAGTC | 11 |
| | R1: 5'-GGCGCGCCCACATAGGAACATTGG CCTGC | 12 |
| | F2: 5'-CCTAGGGCCTTGTCATCGGTTGTGTG | 13 |
| | R2: 5'-GGCGCGCCCTGCTGCCTACACACTT CCTT | 14 | b.

| Mutated Region | Primers | SEQ ID NO: |
|---|---|---|
| TGFBR1 3' UTR | miR-1343 site 1: 5'-GTAATAAAGTCAATTAAAAACTTCCGCGGATTT CTTTGGACCCAGGAAACAG | 33 |
| | miR-1343 site 2: 5'-TCCGCGGATTTCTTTGGACTTAAGAAACAGCCA TGTGGGTCC | 34 |
| | miR-1343 site 3: 5'-GCACTATGAACGCTTCTTTCCGTCGACAGAAAA TGTGTAGTCTAC | 35 |

TABLE 1-continued

Primers used for (a) cloning of 3' UTRs, (b) mutagenesis of miR-1343 seed sequences within cloned 3' UTRs, and (c) SYBR Green qPCR assays.

| | | SEQ ID NO: |
|---|---|---|
| TGFBR2 3' UTR | miR-1343 site: 5'-GAGTTCTCCAATAAAACCAATTTCCGCGGAATATTTGATGTTTTTCCTTGT | 36 |
| ELMO2 UTR | 3' miR-1343 site 1: 5'-GAAGGGAAGGCCAACTTCTCGAGGTCTGGAAGGCCAAAGG | 37 |
| | miR-1343 site 2: 5'-GGTTTTCCCTGCAGCGTTACTAGTGACTTAAGAGGGCAGGA | 38 |
| | miR-1343 site 3: 5'-CAGGCAGCCTTTCCGCGGCCAGCTGTTGCT | 39 |
| | miR-1343 site 4/5: 5'-AGAATGTAAGTGTTTCGCCTAGGCCCAAAATCCCTTCTCCGCGGTACCGTCGTTTCTGG | 40 | c.

| Gene | Primers | SEQ ID NO: |
|---|---|---|
| TGFBR1 | F: 5'-CGGGGAGAAGAAGTTGCTGT | 15 |
| | R: 5'-CACCAACCAGAGCTGAGTCC | 16 |
| TGFBR2 | F: 5'-AATAGGACTGCCCATCCACTG | 17 |
| | R: 5'-TCTCACAGATGGAGGTGATGC | 18 |
| ELMO2 | F: 5'-GGGACATGGTTTCAATCACC | 19 |
| | R: 5'-TCTGGTACAGACTCTGGCTG | 20 |
| ITGA5 | F: 5'-TTACGGCTATGTCACCATCCTT | 21 |
| | R: 5'-CCCCACCAGCAAGTCATCCA | 22 |
| SERPINE1 | F: 5'-CCTCTTCCACAAATCAGACGGC | 23 |
| | R: 5'-CTCTTTTTCATAAGGGGCAGCA | 24 |
| SLC4A7 | F: 5'-ATCTTGGCAAAACTAGCTCAACT | 25 |
| | R: 5'-CGACTCTCTTTACTAAACGGGAC | 26 |
| SMAD2 | F: 5'-CGACACACCGAGATCCTAACA | 27 |
| | R: 5'-ATATCCAGGAGGTGGCGTTT | 28 |
| SMURF1 | F: 5'-TACCAGCGTTTGGATCTATGC | 29 |
| | R: 5'-GCCGGTTCCTATTCTGTCTCG | 30 |
| β2M | F: 5'-CTCTCTCTTTCTGGCCTGGAG | 31 |
| | R: 5'-TCTGCTGGATGACGTGAGTA | 32 |

Transient Transfections and Reporter Assays

Transient transfections of hsa-miR-1343-3p Pre-miR miRNA precursor (PM20896, #AM17100, Life Technologies, LT) and Negative control miRNA precursor #2 (#AM17111, LT) were performed using Lipofectamine RNAiMax or Lipofectamine 2000 (LT) according to the manufacturer protocols to a final concentration of 20 nM.

Dual transient transfections of miRNA precursors plus plasmid DNA (pMIR-Report and pMIR-β-galactosidase, Promega) were performed as described previously (ref.65; herein incorporated by reference in its entirety) using Lipofectamine 2000 (LT) according to the manufacturer's protocol. Cells were lysed 48 hours post-transfection in 1× Reporter Lysis Buffer (Promega). Luciferase assays were performed using the Luciferase Assay System (Promega) and β-galactosidase assays were performed using the β-galactosidase Assay System (Promega) according to standard protocols.

Transient transfections of p3 TP-lux (ref.38; herein incorporated by reference in its entirety) and a modified pRL Renilla vector (Promega) were performed using Lipofectamine 2000 (LT) according to the manufacturer's protocol. Cells were lysed in 1× Passive Lysis Buffer (Promega) and luciferase assays were performed using the Dual Luciferase Reporter Assay System (Promega).

RNA-Sequencing

RNA-seq was carried out as described previously (ref.42; herein incorporated by reference in its entirety).

Cell Adhesion Assays

Cell adhesion assays were completed as described previously (ref.66; herein incorporated by reference in its entirety). Here, 96 well plates were coated with 50 µl of 5 µg/mL Collagen type 1 solution from rat tail (Sigma).

Quantitative PCR

For standard qPCR assays, RNA was isolated from cells using Trizol (LT) by standard protocol 48 hours following miRNA transfection. cDNA reactions were performed using the TaqMan Reverse Transcription Kit (LT) according to the manufacturer instructions. qPCR reactions were completed using Power SYBR Green (LT) and Ct values were normalized against β-2-microglobulin (β2M). See Table 1c for primers.

For miRNA qPCR assays, RNA was isolated from cells using the miRVana miRNA Isolation Kit (LT). miRNAs were reverse transcribed using the miRNA Reverse Transcription Kit (LT) and TaqMan qPCR assays were performed using the hsa-miR-1343-3p TaqMan Assay (LT), normalized to RNU6B (LT).

Western Blot

Cell lysates were analyzed by standard western blot methods. Antibodies were against TGFBR1 (#3712), pSMAD2/3 (#8828), pSMAD3 (#9520), SMAD2/3 (#5678), GAPDH (#5174) (all from Cell Signaling); TGFBR2 (sc-400), E-cadherin (sc-7870), Collagen1a1 (sc-8783) (all from Santa Cruz Biotechnology); ELMO2 (SAB2500350, Sigma-Aldrich); and αSMA (M0851, Dako). Secondary antibodies were against mouse (P0447), rabbit (P0448), or goat (P0449) (all from Dako).

TGF-β Treatment

Cells were serum starved in DMEM supplemented with 0.5% FBS for 6-16 hours prior to TGF-β treatment. Human recombinant TGF-β1 (R&D Systems) was added to a final concentration of 5 ng/mL (unless otherwise noted) in serum-depleted media for a period of 1-48 hours.

Immunofluorescence

Immunofluorescence was completed under standard procedures using a primary antibody against αSMA (M0851, Dako) or SMAD2/3 (#5678, Cell Signaling), and an anti-mouse Alexa-Fluor-549 (715-585-150, Jackson ImmunoResearch) or anti-rabbit Alexa-Fluor-488 (711-545-152, Jackson ImmunoResearch) secondary antibody with DAPI counterstain. Microscopy utilized a Leica DMR-HC Upright microscope and a QImaging Retiga 4000R camera.

Wound Healing Assays

Wound healing assays were performed as previously described (ref 66; herein incorporated by reference in its entirety). Cells were wounded with a p200 pipette tip and observed over a period of 24 hours via microscopy. Scratch area was measured using ImageJ software (NIH).

Cell Proliferation Assays

The total number of viable cells was measured every 24 hours using the CellTiter96 Aqueous Non-Radioactive Cell Proliferation Assay (MTS) (Promega) according to the manufacturer instructions.

Northern Blot

Northern Blots to detect small RNAs were completed by standard protocol. Briefly, RNA was isolated from cells using Trizol (LT) according to the manufacturer instructions.

Twenty micrograms of RNA was run on a 15% polyacrylamide-urea gel, which was then transferred to Zeta Probe GT membranes (BioRad) by capillary action. Membranes were hybridized in ULTRAhyb-Oligo (LT) overnight at 42° C. with DNA probes complementary to miR-1343-3p (5'-GCGAGAGTGCGGGCCCCAGGAG-3' SEQ ID NO: 41)) or U6 small nuclear RNA (5'-CACGATTTGCGTGTCATC-CTT-3' (SEQ ID NO: 42)) that were γ32P end-labeled with T4 polynucleotide kinase (NEB). Membranes were washed twice each in 2×SSC, 0.1% SDS and 2×SSC, 0.5% SDS before being exposed to a phosphoimager screen for several hours to several days. Images were captured using a Typhoon FLA 7000 phosphoimager (GE).

Statistical Analysis and Graphs

All graphs illustrate mean values and error bars denote standard deviation. Statistics were performed using unpaired Student's t tests on Prism software (Graphpad).

Example 2 miR-1343 is Predicted in Silico to Target Both TGF-β Receptors

Figure 1C:
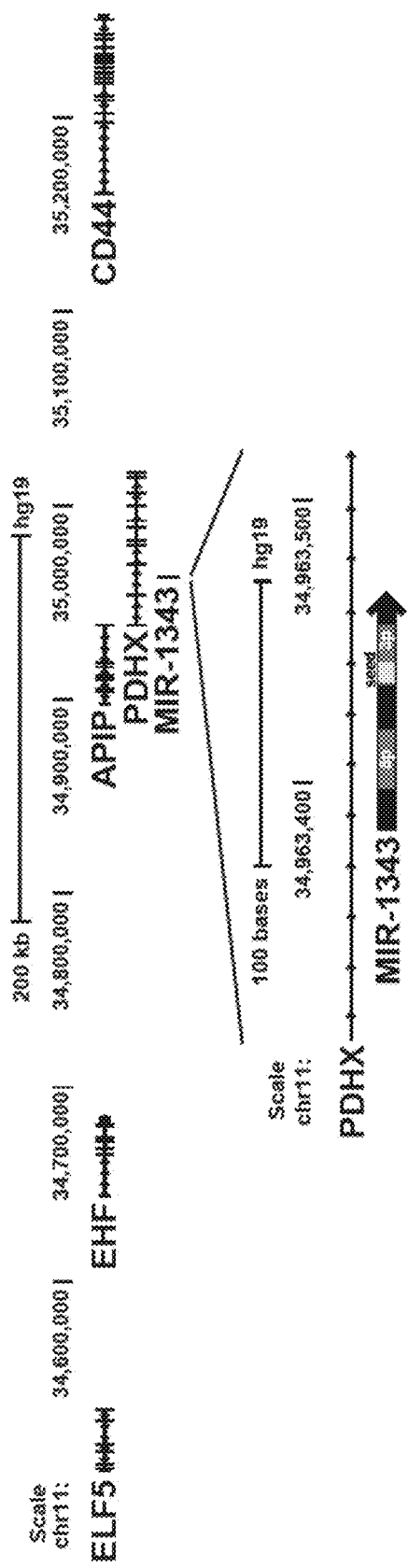

TGF-β signaling is one of the most notable promoters of lung fibrosis. Experiments were conducted during development of embodiments of the present invention to identify miRNAs that directly repress expression of the two receptors that initiate the TGF-β signaling pathway: TGF-β receptor 1 and receptor 2 (TGFBR1, TGFBR2). The majority of miRNAs reduce gene expression post-transcriptionally by binding complementary seed sites located within the 3' UTR of the transcript (ref.33; herein incorporated by reference in its entirety). To identify miRNAs that target both TGFBR1 and TGFBR2 3' UTRs, TargetScan, a miRNA target prediction tool that is recognized as the most comprehensive and least error prone in silico approach, was employed (refs. 33,34; herein incorporated by reference in their entireties). The TGFBR1 3' UTR is 4886 bp long within which TargetScan predicts seed sites for 528 miRNAs. TGFBR2 has a 2543 bp 3' UTR with 360 predicted miRNA targeting sites. Intersection of these 2 data sets showed 175 miRNAs that were predicted to target both genes (FIG. 1a). Less than 20 of these had context scores for both 3' UTRs that were significant enough to warrant further study (<−0.15). Within this group, miR-1343 had top context scores for both TGFBR1 and TGFBR2 (−0.90 and −0.39, respectively) (FIG. 1b). miR-1343 is located within an intron of pyruvate dehydrogenase complex component X (PDHX), a gene mapping to chromosome 11p13. This genomic region was previously shown in a genome wide association study (GWAS) to significantly associate with lung disease severity in CF patients carrying the F508del mutation (32) (FIG. 1c). Because of the major impact of lung fibrosis on disease progression in CF, miR-1343 was a strong candidate for further analysis.

Example 3 miR-1343 Targets the 3' UTRs of TGFBR1 and TGFBR2

Figure 2B:
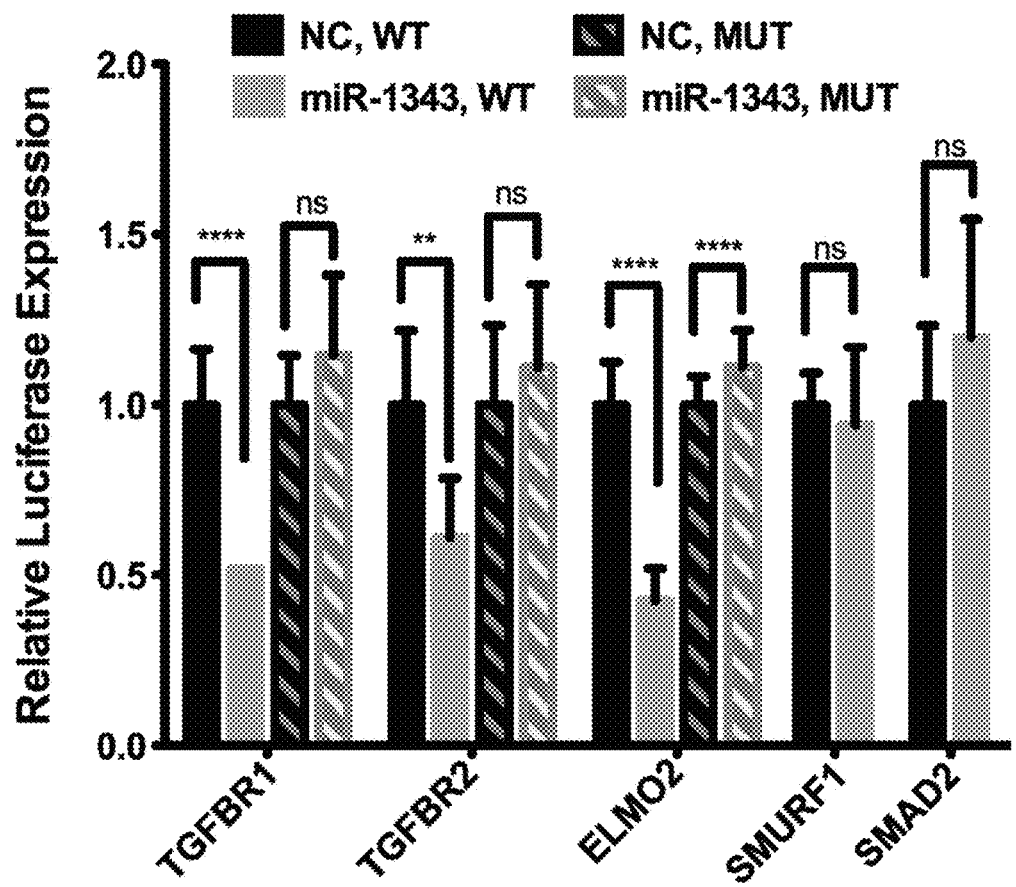

TGFBR1 was the most significant target gene predicted for miR-1343 according to TargetScan (FIG. 1b, 2a). In addition to TGFBR2, SMAD specific E3 ubiquitin ligase (SMURF1), which acts as a negative regulator of TGF-β signaling, was also a predicted miR-1343 target (context score −0.28). Other genes with high context scores that were relevant to lung biology and fibrosis included Engulfment and cell motility (ELMO2, −0.89), Collagen, type V, alpha 1 (COL5A1, −0.70) and Integrin alpha 5 (ITGA5, −0.62), among others (FIG. 2a).

Figure 8:
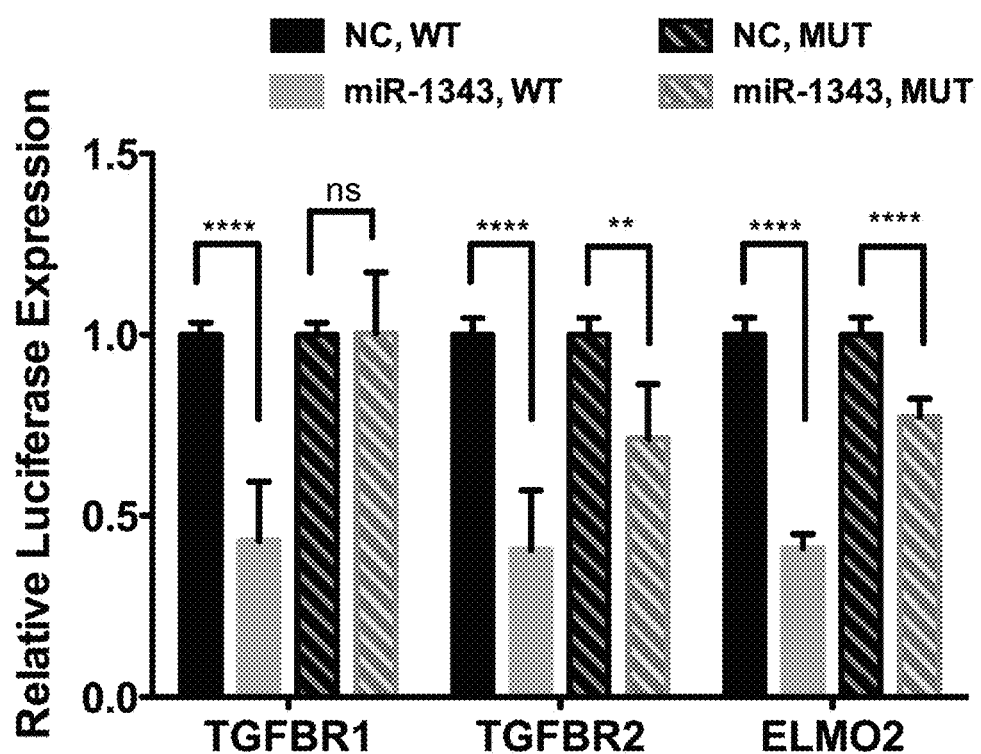
FIG. 8: Luciferase assay of Caco2 cells transiently transfected with pMIR-REPORT-3' UTR constructs. Cells were transfected with either wild type (WT) or mutant (MUT) pMIR-REPORT-3' UTR constructs along with pre-miR-1343 or negative control (NC).

To establish whether miR-1343 targeted the 3' UTRs of TGFBR1, TGFBR2, ELMO2, and SMURF1, these were cloned into the pMIR-Report vector downstream of a luciferase reporter gene. Luciferase expression from this vector decreases if the 3' UTR is a target of the miRNA. Also included in these assays was the TGF-β effector SMAD2, which though a predicted target of miR-1343, has a very small context score (>0.02). The constructs were transiently transfected into A549 lung adenocarcinoma cells with precursor (pre)-miR-1343 or a non-targeting negative control (NC) miRNA. Luciferase activity was assayed 48 hours post-transfection and normalized to a β-galactosidase transfection control (FIG. 2b). miR-1343 significantly reduced luciferase expression from the TGFBR1, TGFBR2, and ELMO2 3' UTR constructs in comparison to the NC miRNA. Mutation of the miR-1343 seed sites in TGFBR1, TGFBR2 and ELMO2 FIG. 7) abolished this repression, demonstrating specific targeting by miR-1343. Additionally, miR-1343 had no impact on luciferase expression from the SMAD2 and SMURF1 3' UTR constructs. Direct targeting of the 3' UTR of TGFBR1, TGFBR2, and ELMO2 was confirmed in Caco2 intestinal epithelial cells FIG. 8). These results indicate that miR-1343 reduces expression of both TGF-β receptors through direct targeting of their 3' UTRs.

Figure 2C:
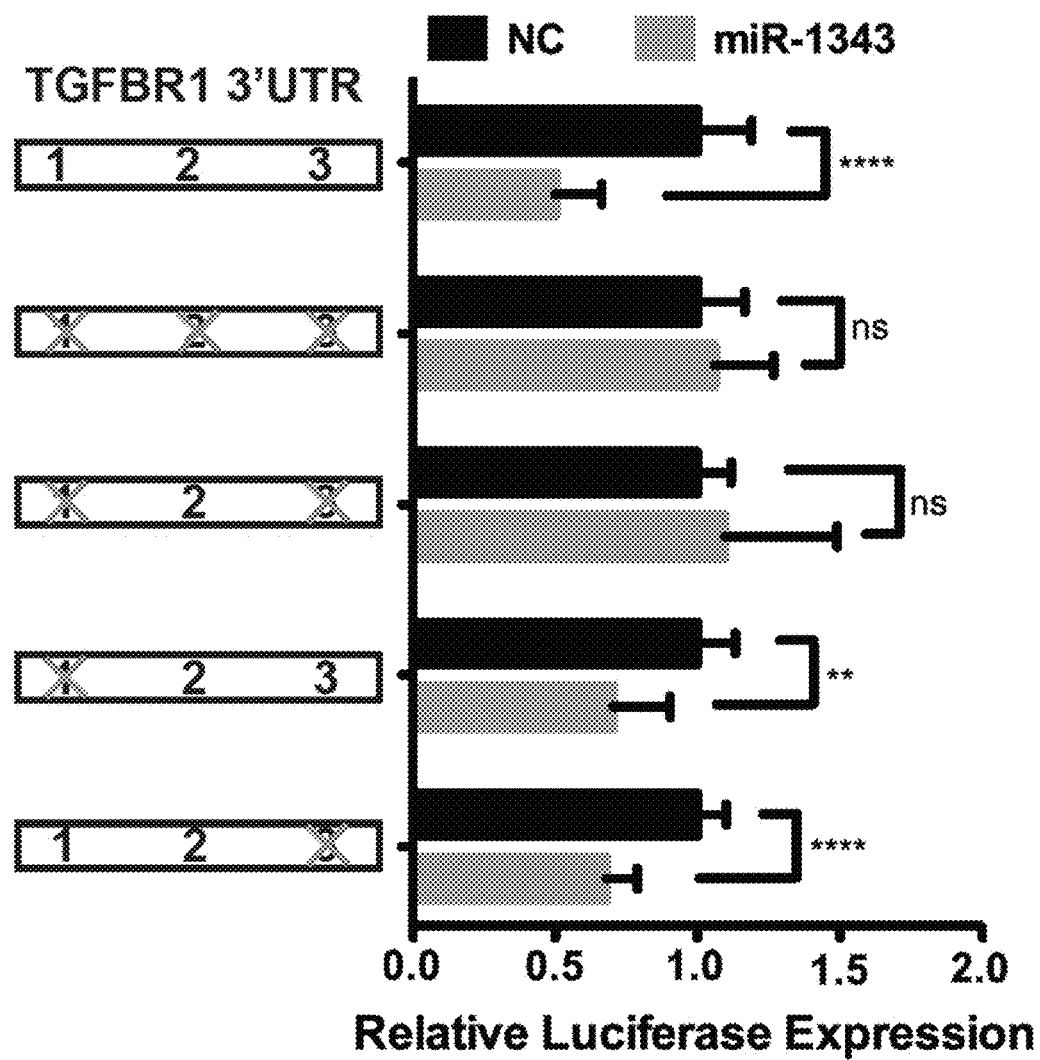

TGFBR1 contains three miR-1343 seed sites in its 3'UTR (FIG. 2a), with sites 1 and 3 scored by TargetScan as well conserved, while site 2 is non-conserved. A combination of seed site mutants were created within the pMIR-Report-TGFBR1 3' UTR construct, with all 3 sites destroyed or sites 1 and 3 mutated individually or together (FIG. 2c and FIG. 7). Using the same transfection protocol described above, mutation of all three miR-1343 sites abolished the impact of the miRNA on the TGFBR1 3' UTR, as did combined destruction of sites 1 and 3. Single site mutations of either site 1 or site 3 alone still retained the effect of miR-1343. These data indicate that these two conserved sites enable full miR-1343 targeting.

Example 4 miR-1343 Controls the Expression of Genes Important for Lung Health and Disease

Figure 3A:
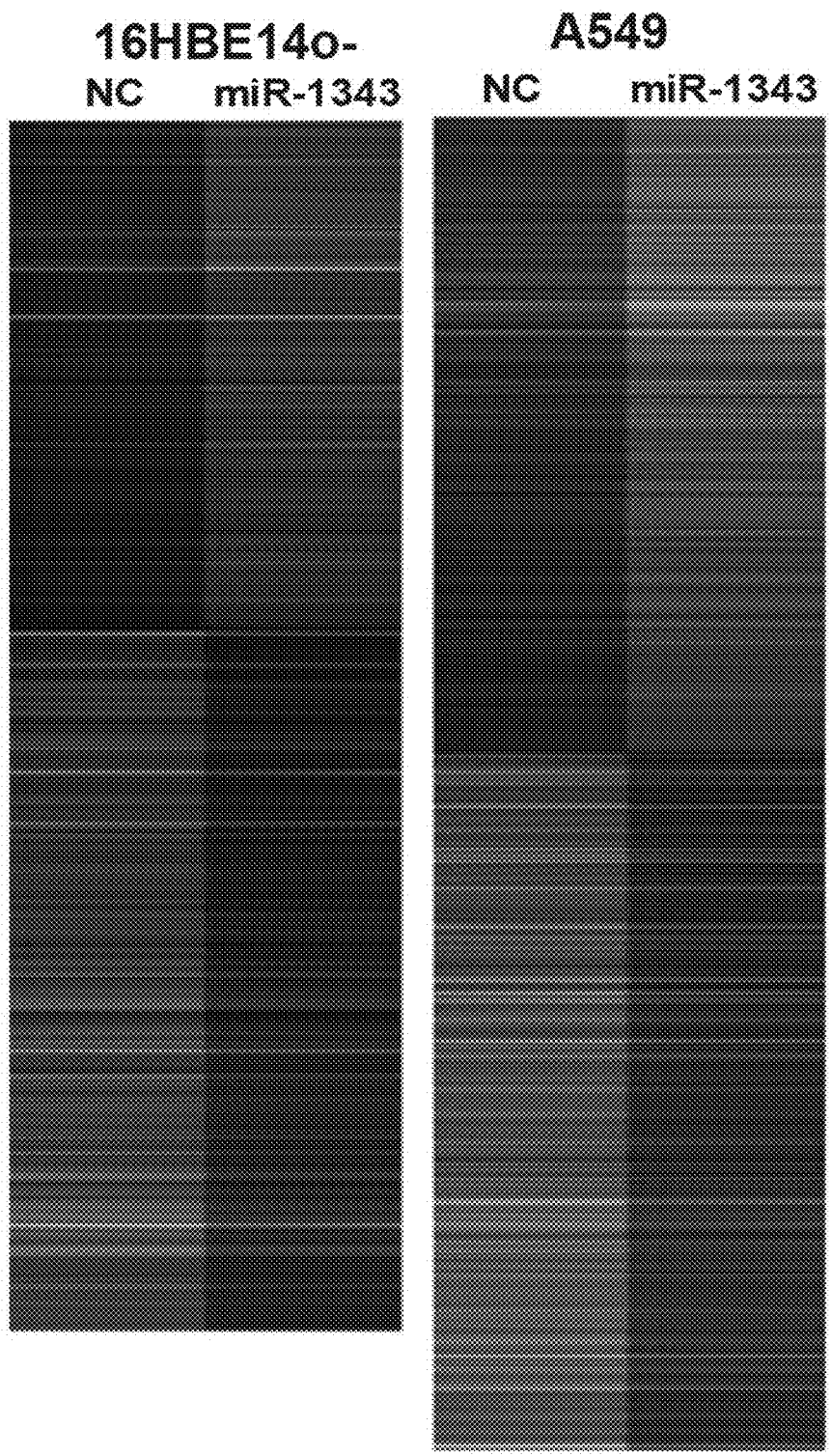
Figure 3B:
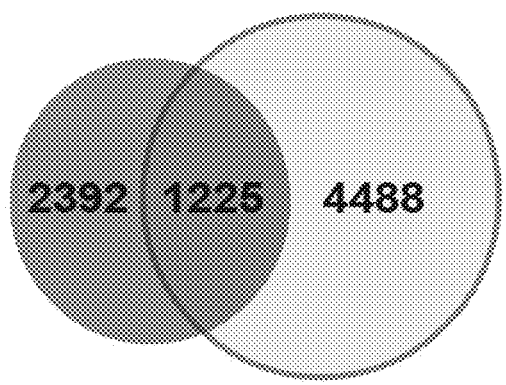

Since miRNAs often control biological processes at multiple levels, the impact of miR-1343 was investigated genome-wide by RNA-sequencing (RNA-seq). Pre-miR-1343 or NC miRNA were transiently overexpressed in A549 and 16HBE14o-lung epithelial cells. Total RNA was extracted 48 hours post-transfection from 4 miR-1343 and 4 NC miRNA samples and RNA-seq was performed on libraries generated from them. Tophat and Cufflinks software were used with default parameters to generate fragments per kilobase per million mapped fragments (FPKM) values and CuffDiff was used to determine differentially expressed genes (DEGs) (ref.35; herein incorporated by reference in its entirety). Transcripts of 4488 genes in A549 cells and 2393 genes in 16HBE14o-cells showed significant changes following miR-1343 overexpression compared to NC cells (FIG. 3a) (GEO: Accession # pending). Of these, 1225 were differentially expressed in both cell types (FIG. 3b) with 713 decreasing and 391 increasing in the miR-1343 transfected cells. The remaining genes (121) showed opposite responses in the 2 cell types.

Figure 3C:
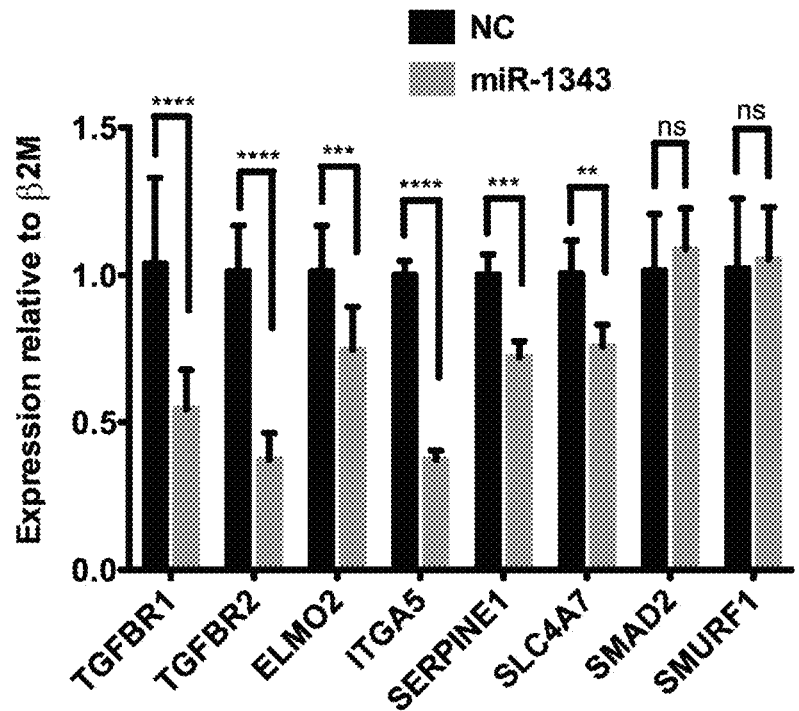
Figure 9:
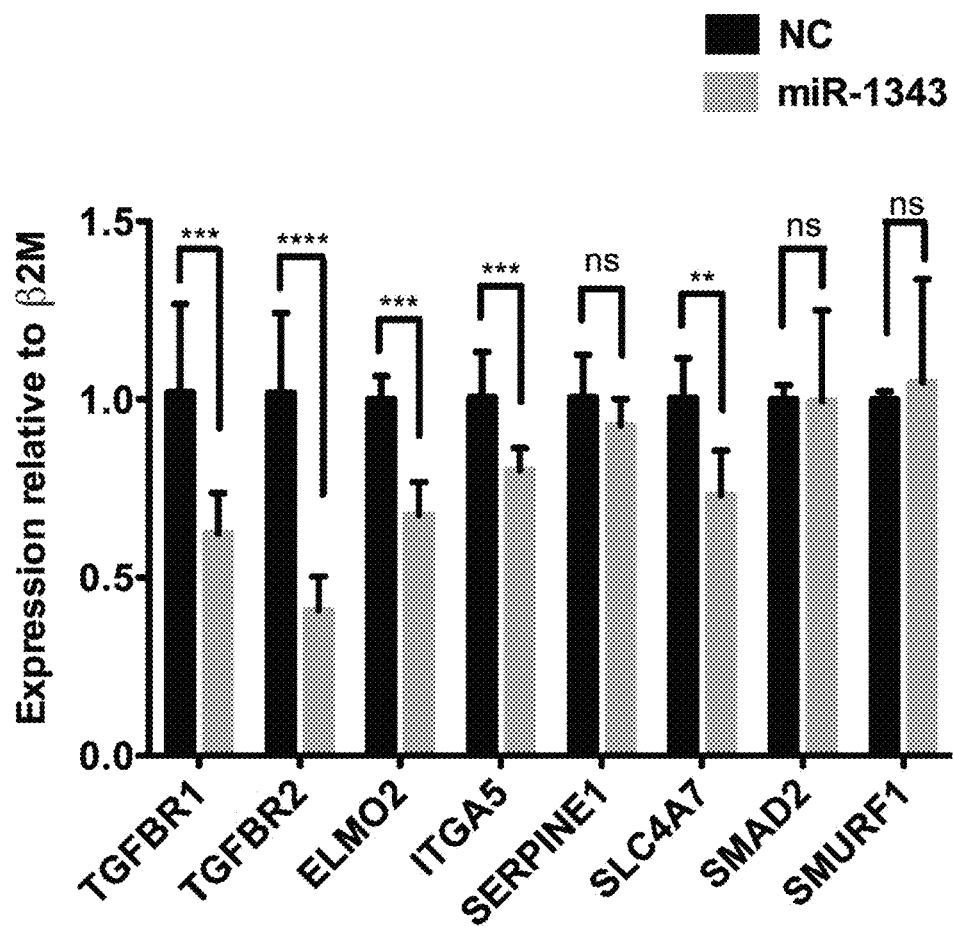
FIG. 9: Gene expression levels in 16HBE14o-cells transiently transfected with pre-miR-1343 or negative control (NC) miRNA. RNA was extracted after 48 hours. RT-qPCR Ct values were normalized to beta-2-microglobulin.
Figure 10:
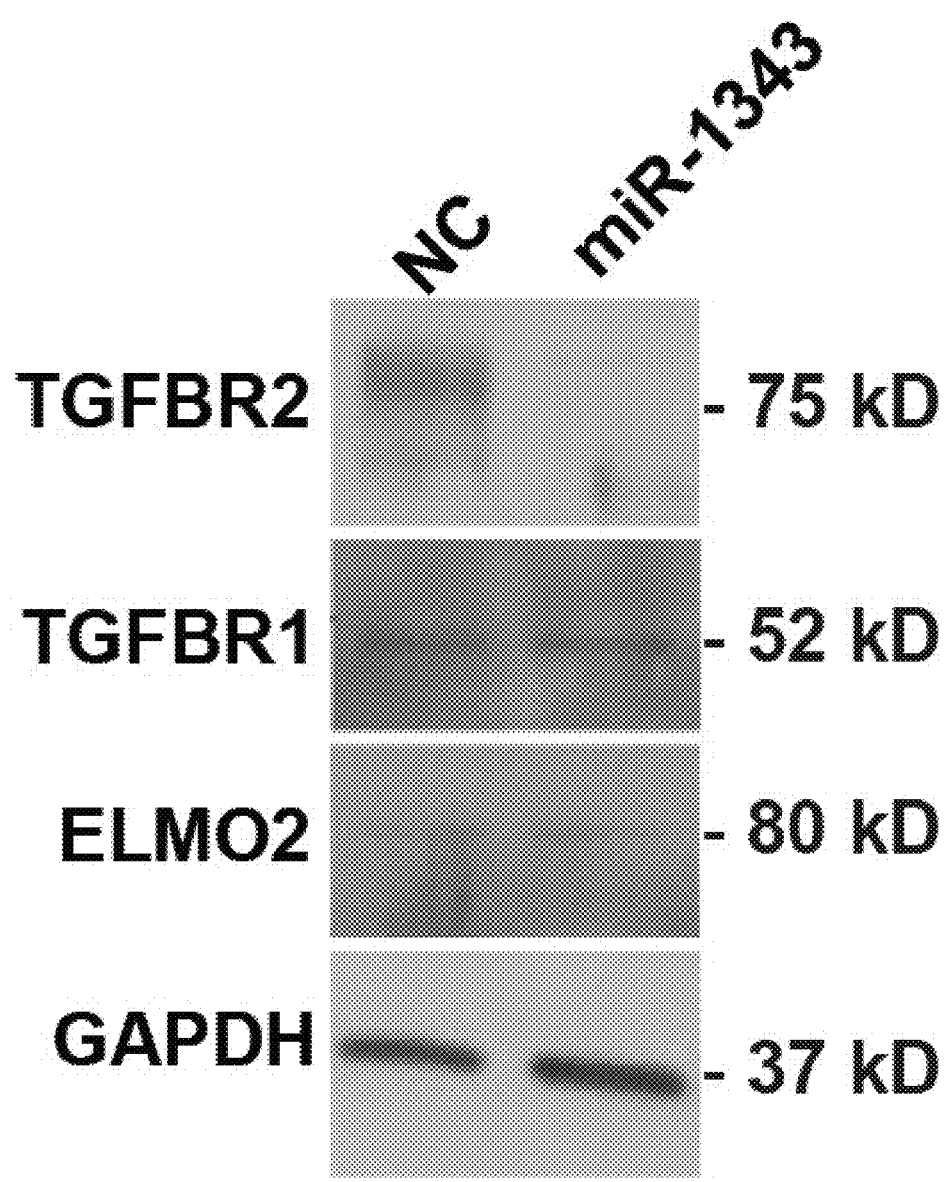
FIG. 10: Western blot of 16HBE14o-lysates transfected with pre-miR-1343 or negative control (NC) miRNA. Cells were lysed after 48 hours and probed with antibodies specific to TGFBR1, TGFBR2 and ELMO2. GAPDH was the loading control.

Overlapping the DEGs identified by RNA-seq with TargetScan-predicted miR-1343 targets yielded 96 genes in common, all of which likely represent true miR-1343 target genes. TGFBR1, TGFBR2, ELMO2, and ITGA5 were among those common genes and consistent with luciferase reporter gene assays (FIG. 2b) SMAD2 and SMURF1 were not among the DEGs. Genes identified by both RNA-seq and TargetScan were further validated by reverse transcription and quantitative polymerase chain reaction (RT-qPCR) assays following NC or pre-miR-1343 transient expression in A549 cells (FIG. 3c). Levels of TGFBR1, TGFBR2, ELMO2, and ITGA5 transcripts were significantly down-regulated in the presence of miR-1343 compared to the NC miRNA. Two additional genes that were differentially expressed by RNA-seq but were not predicted by TargetScan (suggesting they are indirect targets) were also confirmed by RT-qPCR: serpin peptidase inhibitor, Glade E (SERPINE1), a known TGF-β-responsive gene, and solute carrier family 4, member 7 (SLC4A7), a sodium bicarbonate transporter. Also consistent with RNA-seq and luciferase assay results, levels of SMAD2 and SMURF1 transcript were unaffected. Similar data for 16HBE14o-cells are shown in FIG. 9.

Figure 3D:
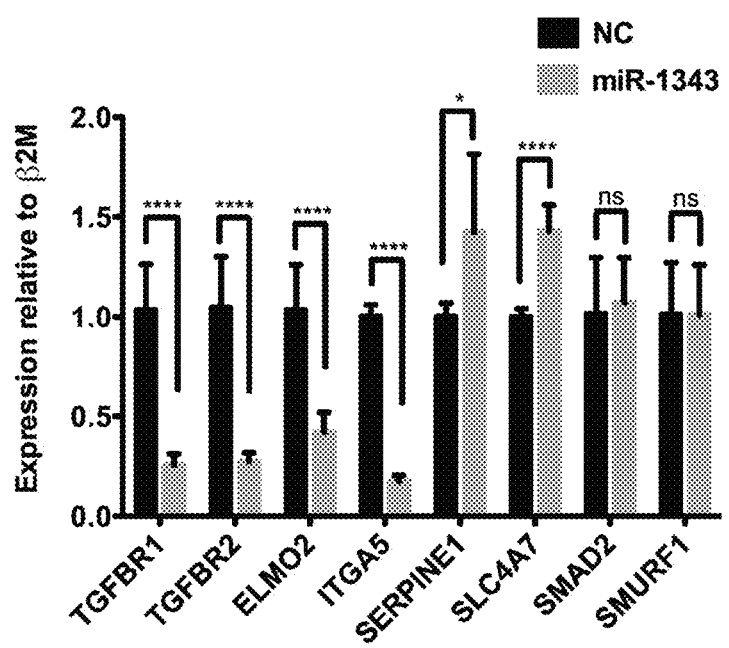

To confirm that the effects of miR-1343 were not limited to lung epithelial cells miR-1343 and NC miRNA were transiently transfected into primary lung fibroblasts (FIG. 3d). Again TGFBR1, TGFBR2, ELMO2, and ITGA5 expression levels were significantly decreased with pre-miR-1343 compared to the NC, while SMAD2 and SMURF1 levels were unaltered. However, in contrast to A549, SERPINE1 and SLC4A7 expression increased in the primary lung fibroblasts. These observations, together with those from 16HBE14o-cells, indicate genes indirectly targeted by miR-1343 can differ between cell types.

Figure 3E:
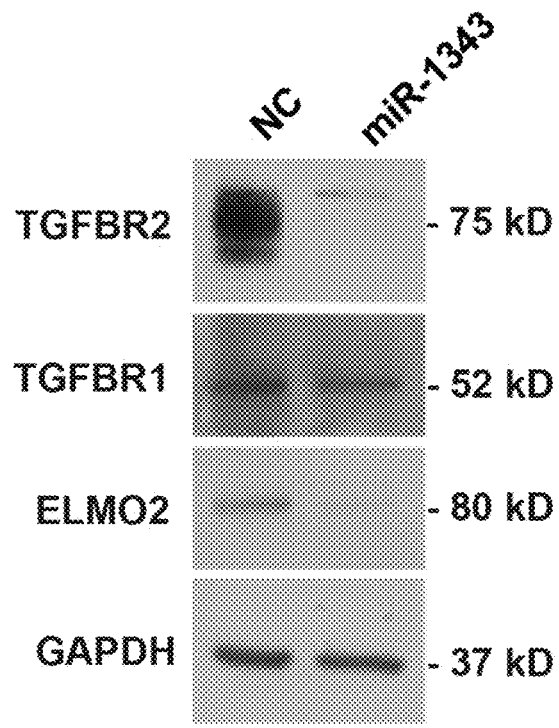
Figure 3F:
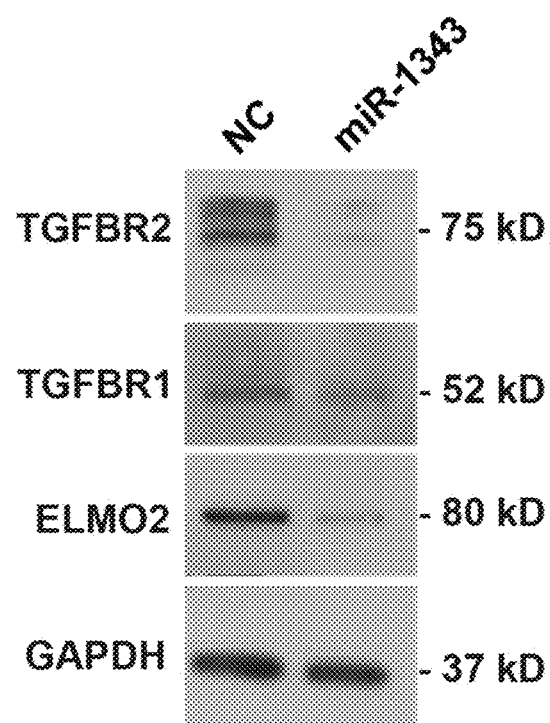

Since miRNAs can destabilize transcripts by several mechanisms, the effects of miR-1343 on the proteins encoded by its target genes was examined. Forty-eight hours after transient transfection of A549 cells with pre-miR-1343 or NC miRNA, cells were lysed and proteins separated by SDS/PAGE followed by western blot. Blots were probed with antibodies specific for TGFBR1, TGFBR2, and ELMO2 and normalized to glyceraldehyde 3-phosphate dehydrogenase (GAPDH) as a loading control (FIG. 3e). TGFBR2 showed substantial down-regulation of expression in miR-1343 treated cells compared to NC miRNA, while TGFBR1 and ELMO2 both showed a lesser reduction. Equivalent results were obtained when protein levels were evaluated after miR-1343 delivery in primary lung fibroblasts (FIG. 3f) and 16HBE14o-cells (Supplementary FIG. 4). These results indicate that miR-1343 regulates critical cellular processes.

Figure 11:
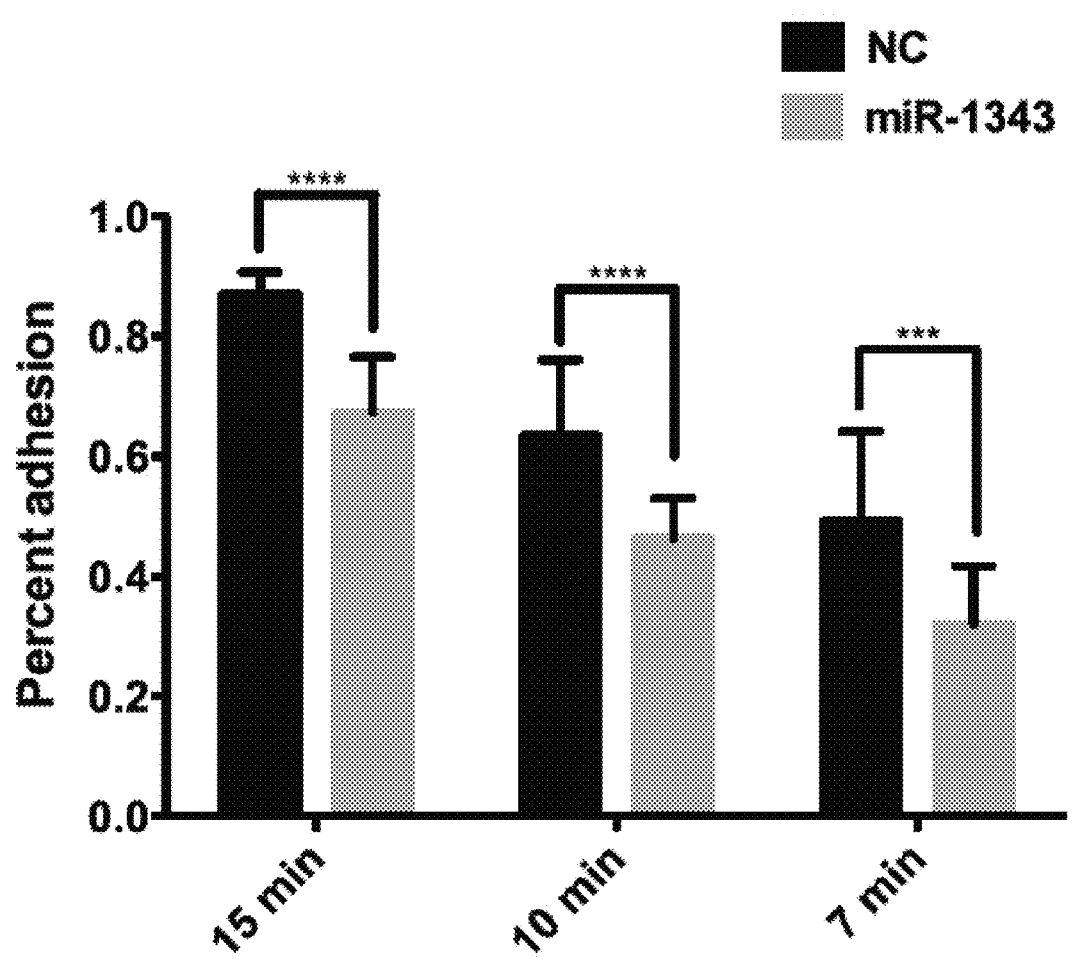
FIG. 11: Adhesion of A549 cells transiently transfected with pre-miR-1343 or negative control (NC) miRNA for 48 hours.

A gene ontology process enrichment analysis was performed on the DEGs that exhibited shared expression changes by RNA-seq in both airway cell lines using the Database for Annotation, Visualization, and Integrated Discovery (DAVID) (refs. 36,37; herein incorporated by reference in their entireties). Among the DEGs down-regulated by miR-1343, pathways involved in lung epithelial function relating to cell growth, cell-substrate junction, and cellular adhesion were significantly altered (FIG. 3g). Consistent with these bioinformatic predictions, cell adhesion assays on Collagen I-coated substrates showed that pre-miR-1343 significantly reduced adhesion of transfected A549 cells in comparison to NC miRNA at multiple different time points FIG. 11). Pathways involved in steroid/lipid biosynthesis and intracellular protein transport were overrepresented among DEGs up-regulated by miR-1343 (FIG. 3h). These results indicate that miR-1343 regulates, both directly and indirectly, multiple cellular processes that are key to lung epithelial function.

Example 5 miR-1343 Perturbs the Canonical TGF-β Signaling Pathway

Figure 4A:
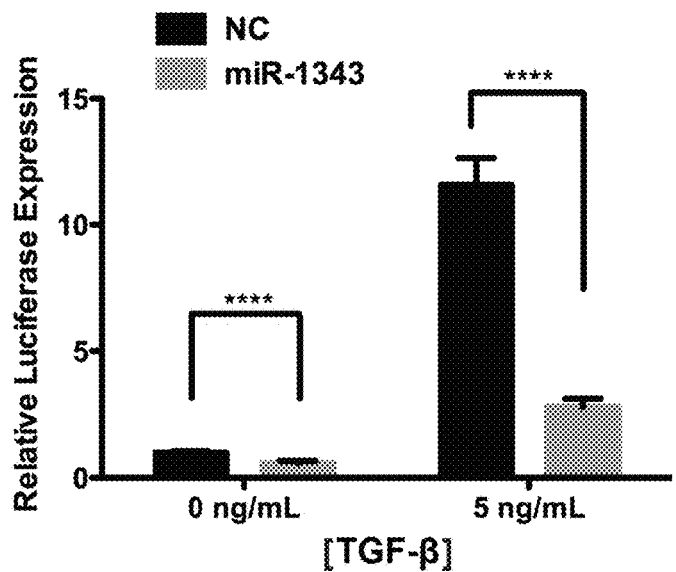
Figure 4B:
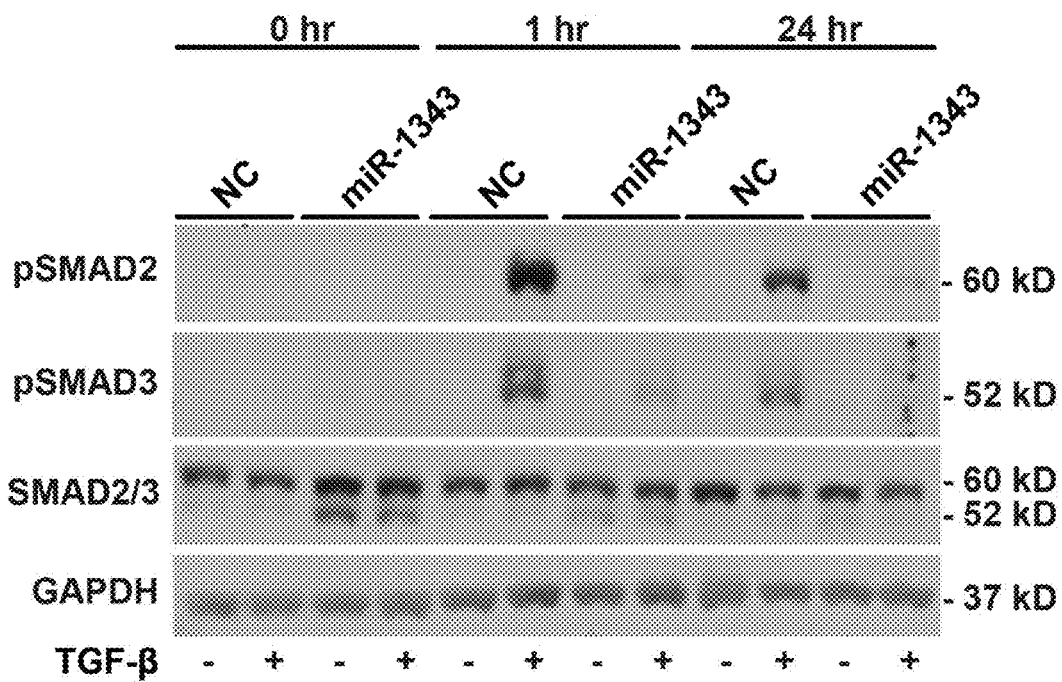

Since miR-1343 targeted and repressed both of the TGF-β receptors in vitro, it was investigated whether this miRNA could influence the TGF-β signaling pathway. First, the p3TP-lux vector was used, which contains a portion of the SERPINE1 promoter and three TGF-β-activated TPA responsive elements driving luciferase expression (ref.38; herein incorporated by reference in its entirety). Pre-miR-1343 or NC miRNA were transfected into A549 cells with p3TP-lux and a *Renilla* transfection control vector. After 48 hours, cells were treated with TGF-$β_1$ to induce the TGF-β signaling pathway (FIG. 4a). TGF-β stimulation of luciferase expression in cells treated with miR-1343 was only 25% of the levels seen in NC miRNA-treated cells. This robust effect suggests that miR-1343 reduces TGF-β signaling in these cells, and that its activity diminishes TGF-β-responsive gene expression.

Figure 12:
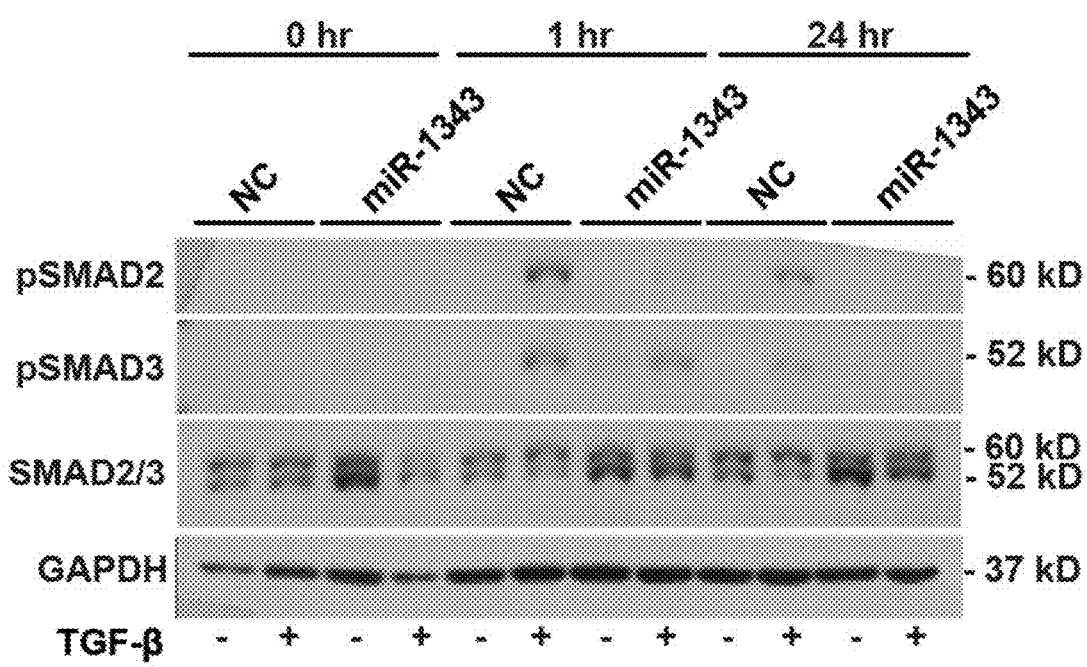
FIG. 12: miR-1343 represses phosphorylation of SMAD2/3.

In its canonical signaling pathway, TGF-β binds to TGFBR1 and TGFBR2, which then dimerize to activate Receptor-SMAD factors (R-SMADs, SMAD2 and SMAD3) by receptor serine kinase activity. Phosphorylated R-SMADs colocalize with the Common-SMAD (Co-SMAD, SMAD4) in the cytoplasm, which promotes R-SMAD translocation to the nucleus where it impacts gene expression (ref 39; herein incorporated by reference in its entirety). To determine if miR-1343 reduces TGF-β signaling by this mechanism, the endogenous cellular pathway was investigated by monitoring phosphorylation and hence activation of SMAD2 and SMAD3 (pSMAD2, pSMAD3). Pre-miR-1343 or NC miRNA were transiently transfected into A549 cells, which after 48 hours, were exposed to TGF-$β_1$ for 1 or 24 hours. Cell lysates were resolved on SDS/PAGE and western blots probed with antibodies specific for pSMAD2, pSMAD3, or total SMAD2/3 (FIG. 4b). miR-1343 substantially reduced the ratio of pSMAD2 and pSMAD3 to total SMAD2/3 after 1 and 24 hours of TGF-β treatment in comparison to NC miRNA. Total SMAD2/3 levels were unchanged. Identical results were obtained when this experiment was repeated in primary lung fibroblasts (FIG. 12).

Because TGF-$β_1$ activation/phosphorylation of SMAD2 and SMAD3 causes their nuclear translocation, it was investigated whether the reduced levels of pSMAD2/3 observed in miR-1343 transfected cells correlated with a lack of their translocation to the nucleus. A549 cells were transiently transfected with pre-miR-1343 or NC miRNA for 48 hours. Cellular localization of total SMAD2/3 was examined by immunofluorescence, after either TGF-$β_1$ treatment (50 ng/mL) or serum starvation conditions for 1 hour (FIG. 4c). In the absence of TGF-β, both NC and miR-1343 cells showed diffuse SMAD2/3 localization throughout the cytoplasm. As expected, TGF-$β_1$ treatment in NC cells induced the nuclear translocation of SMAD2/3; however, this movement was largely abolished in miR-1343 containing cells. These data demonstrate the potent effects of miR-1343 on the canonical TGF-β signaling pathway.

Example 6 miR-1343 Represses Pathways of TGF-β-Induced Fibrosis

Figure 5A:
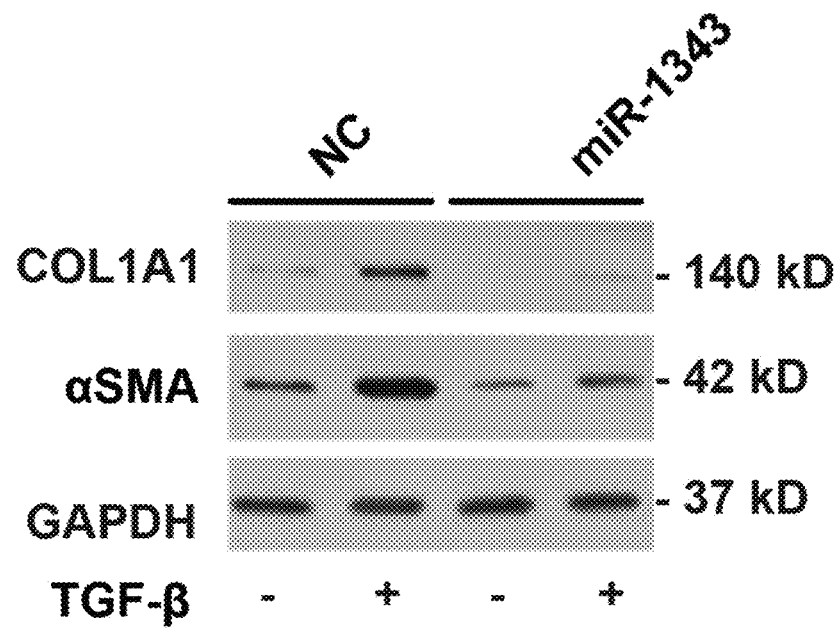
FIGS. 5A-E: Phenotypes associated with TGF-β-induced fibrosis are repressed in miR-1343 overexpressing cells (A) Western blot of lysates from primary lung fibroblasts transiently transfected with miR-1343 or negative control (NC) miRNA and treated with TGF-β$_1$ (5 ng/mL, +) or vehicle control (-) for 48 hours. Blots were probed with antibodies specific for Collagen type I A1 (COL1A1) and alpha smooth muscle actin (αSMA). GAPDH was the loading control. (B) miR-1343 impairs synthesis and structural organization of αSMA after TGF-β exposure. Representative images of immunofluorescence in primary lung fibroblasts transiently transfected with miR-1343 or NC miRNA and treated with TGF-β$_1$ (5 ng/mL, +) or vehicle control (-) for 48 hours. Fluorescence shows αSMA and DAPI is the nuclear counterstain. Merge illustrates αSMA staining plus DAPI. Scale bar=250 µm. (C) Western blot of lysates from A549 cells transiently transfected with miR-1343 or NC miRNA and treated with TGF-β$_1$ (5 ng/mL, +) or vehicle control (-) for 48 hours. Blots were probed with antibodies specific for Epithelial-cadherin (E-cad). GAPDH was the loading control. (D) Representative images of wound scratch assay in A549 cells transiently transfected with miR-1343 or NC miRNA and treated with TGF-β$_1$ (5 ng/mL, +) or vehicle control (-). TGF-β was added at the 0 hour time point when the scratch was created. Cells were imaged again 24 hours post-scratch wounding. Scale bar=0.5 mm. (E) Quantitation of change in wound closure area between 0 and 24 hours of A549 cells described in (D). **** p≤0.0001.
Figure 5C:
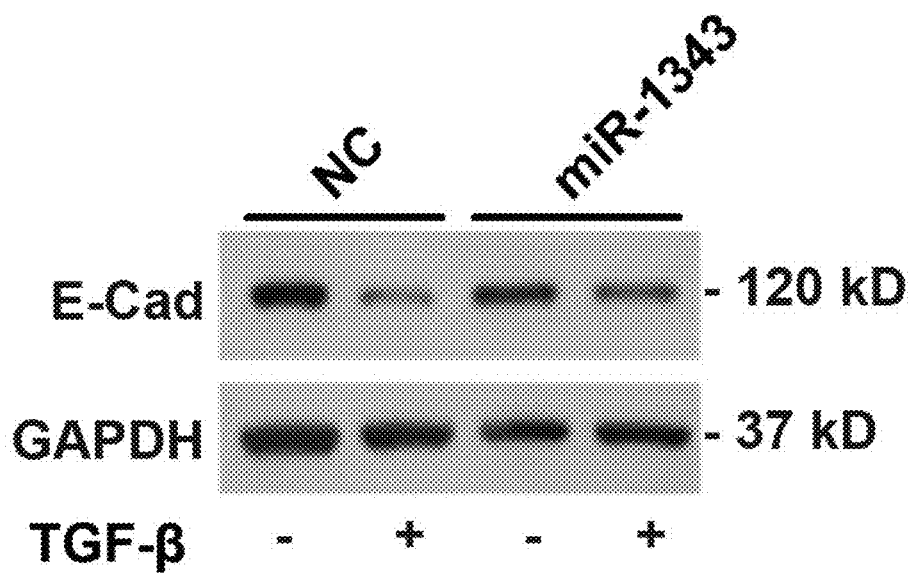
Figure 5B:
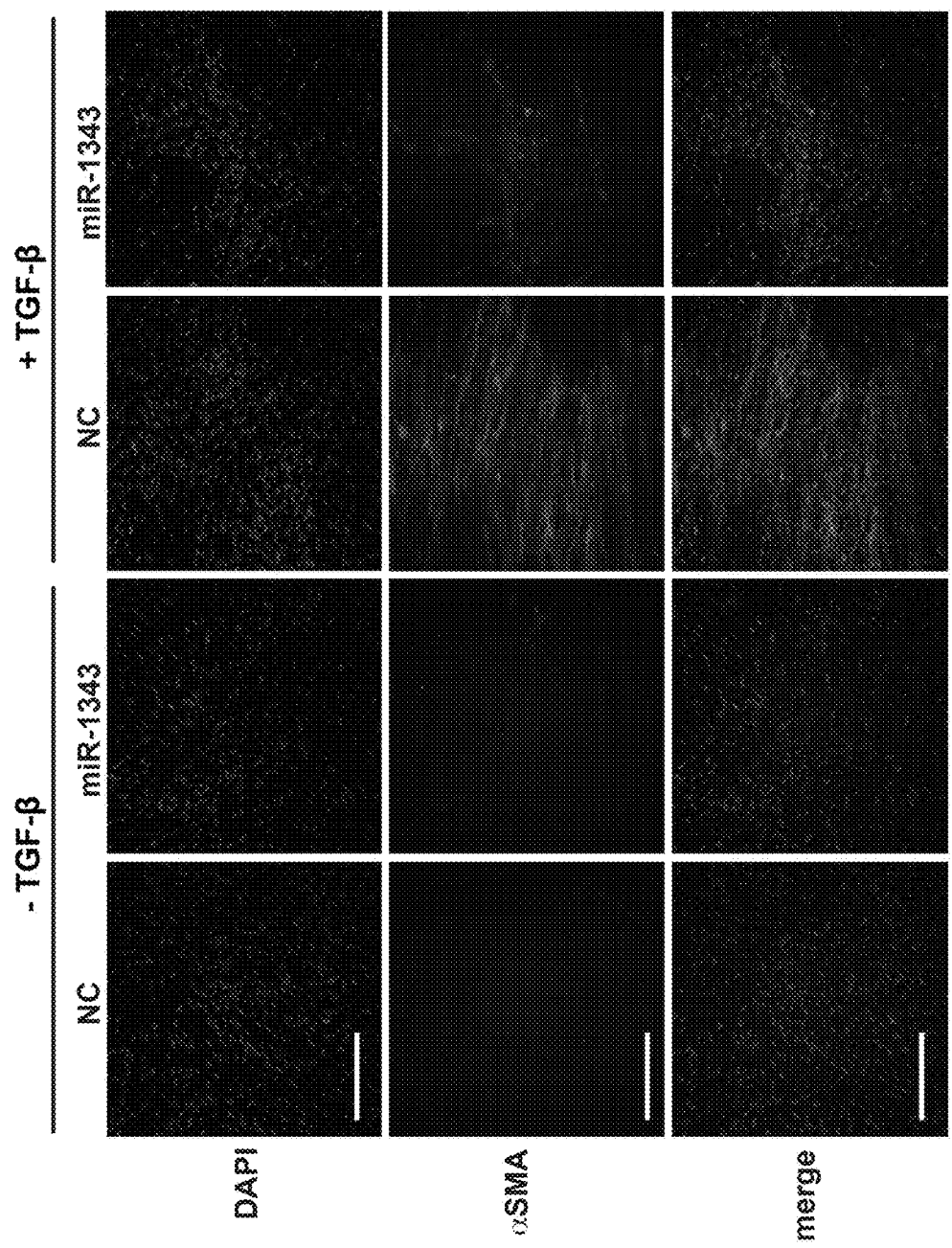
Figure 13:
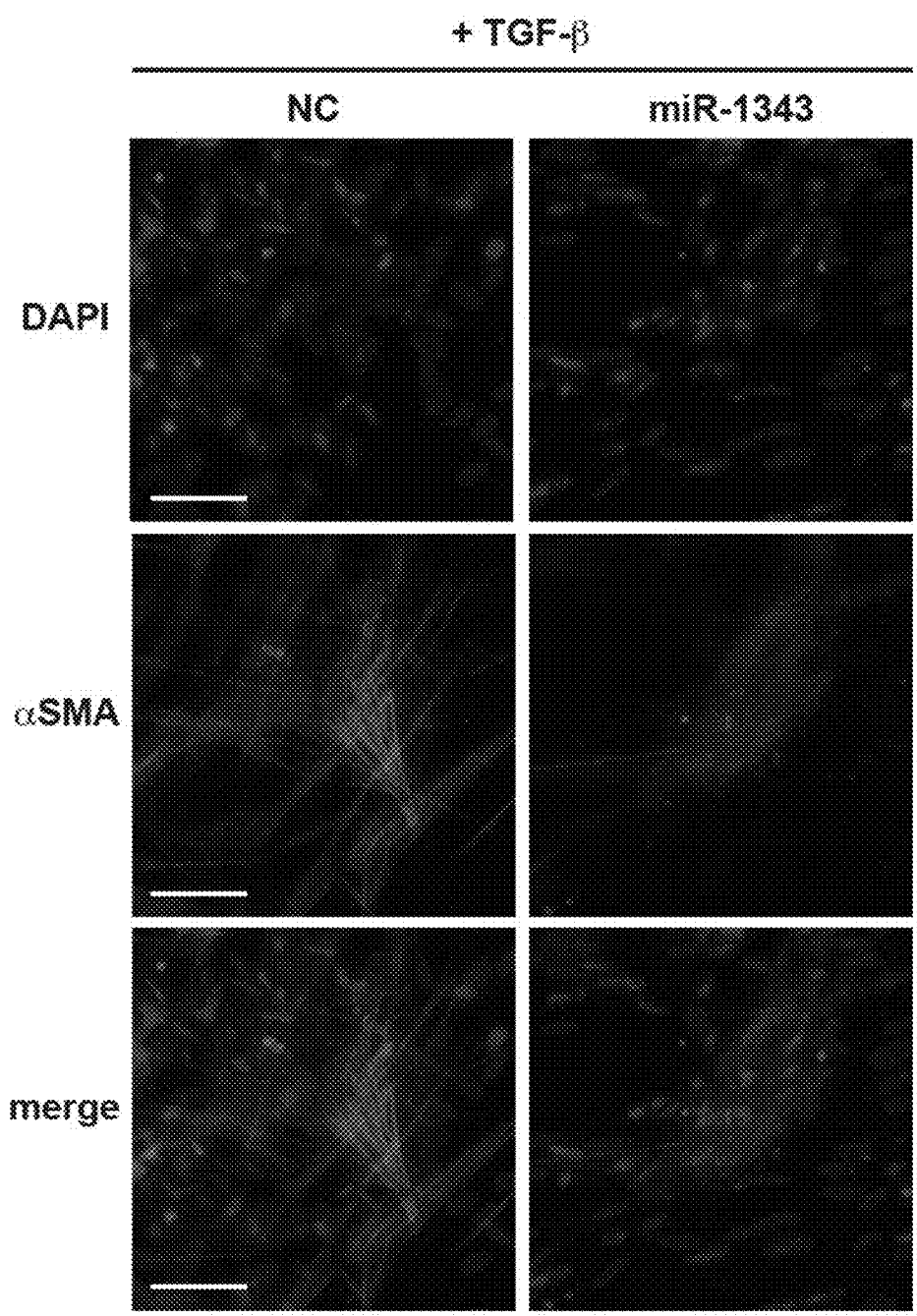
FIG. 13: miR-1343 impairs synthesis and structural organization of αSMA after TFG-β exposure.

Experiments were conducted during development of embodiments of the present invention to determine whether phenotypes associated with TGF-β-induced fibrosis are also influenced by miR-1343; Collagen type I, alpha 1 (COL1A1) and Alpha smooth muscle actin (αSMA) were focused on. These are both structural protein markers of active myofibroblasts and are known to be induced by TGF-β (ref.40; herein incorporated by reference in its entirety=). Primary lung fibroblasts were transiently transfected with pre-miR-1343 or NC miRNA and treated with TGF-$β_1$ for 48 hours. Cell lysates were separated by SDS/PAGE and western blots probed with specific antibodies for each protein, or GAPDH as a control (FIG. 5a). TGF-β induced the expression of both COL1A1 and αSMA in NC miRNA-treated fibroblasts, demonstrating the transition of the lung fibroblasts to an active myofibroblast-like state. In contrast, induction of COL1A1 and αSMA were substantially attenuated in the miR-1343 treated cells. Expression of αSMA protein following TGF-β treatment was also investigated by immunofluorescence in primary lung fibroblasts (FIG. 5b and FIG. 13). After TGF-β exposure, extensive fibers of αSMA were seen in NC miRNA treated fibroblasts. However, in the presence of miR-1343, intracellular αSMA structures were disrupted and the small amounts of protein remaining became diffuse. These results indicate that miR-1343 represses phenotypes associated with TGF-β-induced transition of resident fibroblasts to disease-causing myofibroblasts in the lung.

Another cellular process that is directly induced by TGF-β is cancer-associated epithelial-to-mesenchymal transition (EMT). During EMT, Epithelial-cadherin (E-cad) relocates from epithelial cell-cell junctions and becomes cytoplasmic, thus allowing cells to become more motile, a characteristic of mesenchymal cell types. This process was observed previously in A549 cells, where it is also associated with reduced levels of E-cad (ref.41; herein incorporated by reference in its entirety). To test whether miR-1343 affects TGF-β-induced EMT, A549 cells were transiently transfected with pre-miR-1343 or NC miRNA and treated with TGF-$β_1$ for 48 hours. Cell lysates were resolved on SDS/PAGE and E-cad levels examined by western blot with a specific antibody (FIG. 5c). NC miRNA-treated cells showed greatly reduced levels of E-cad when treated with TGF-β; however, this reduction was less evident in miR-1343-treated cells.

Since mesenchymal cells exhibit increased motility, the migration of A549 cells into a scratch wound following miRNA transient transfection was assessed. Forty-eight hours after pre-miR-1343 or NC miRNA transfection, EMT was induced by TGF-$β_1$ stimulation.

Figure 5D:
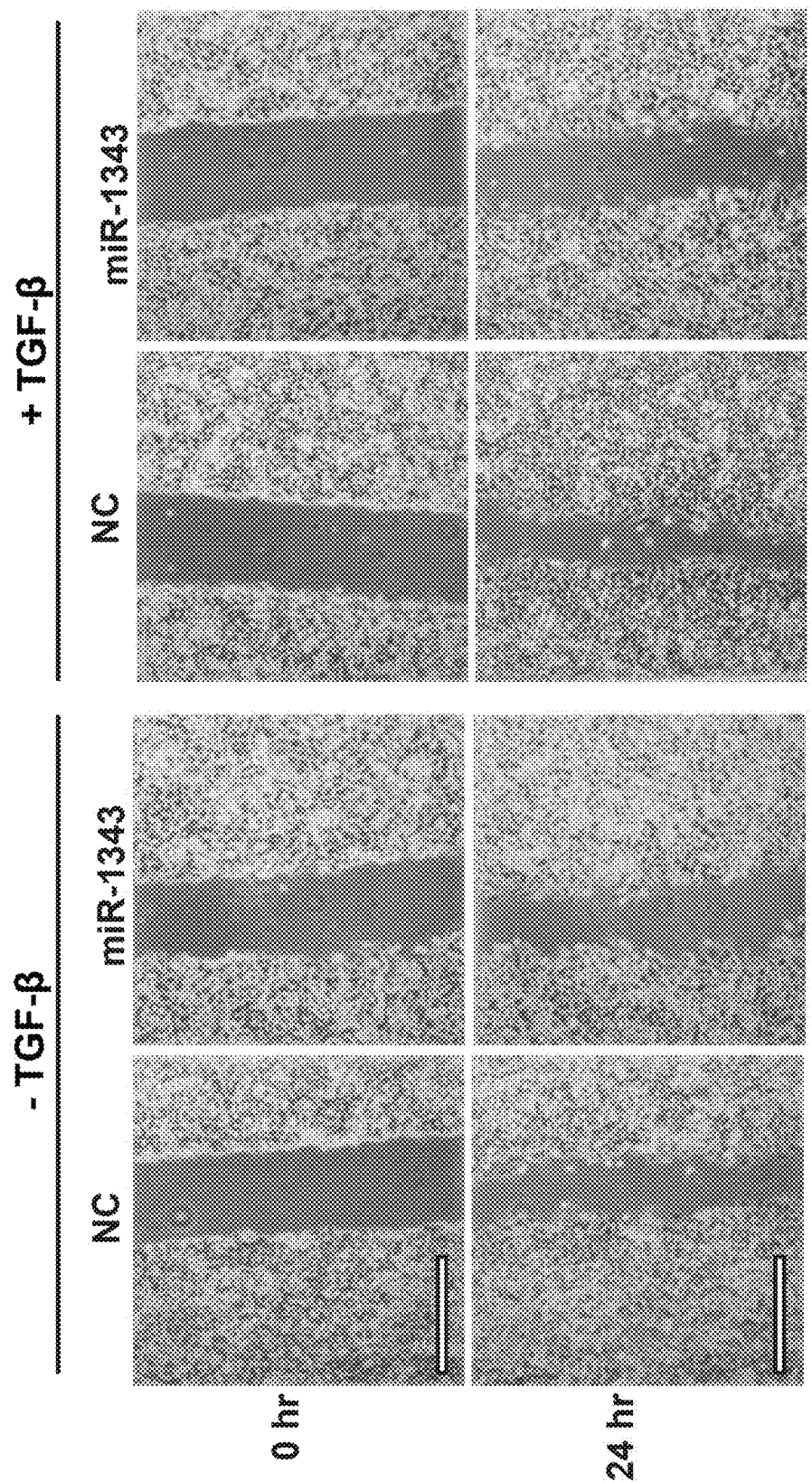
Figure 5E:
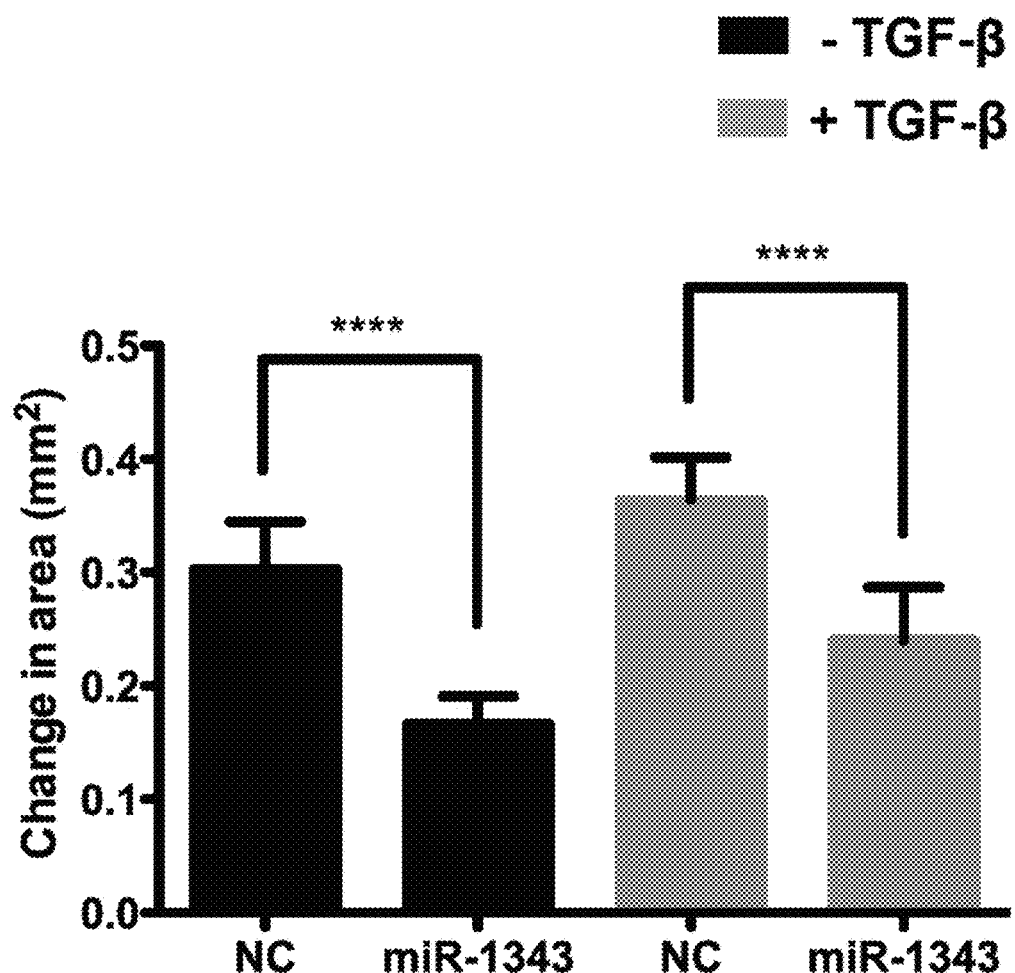
Figure 14:
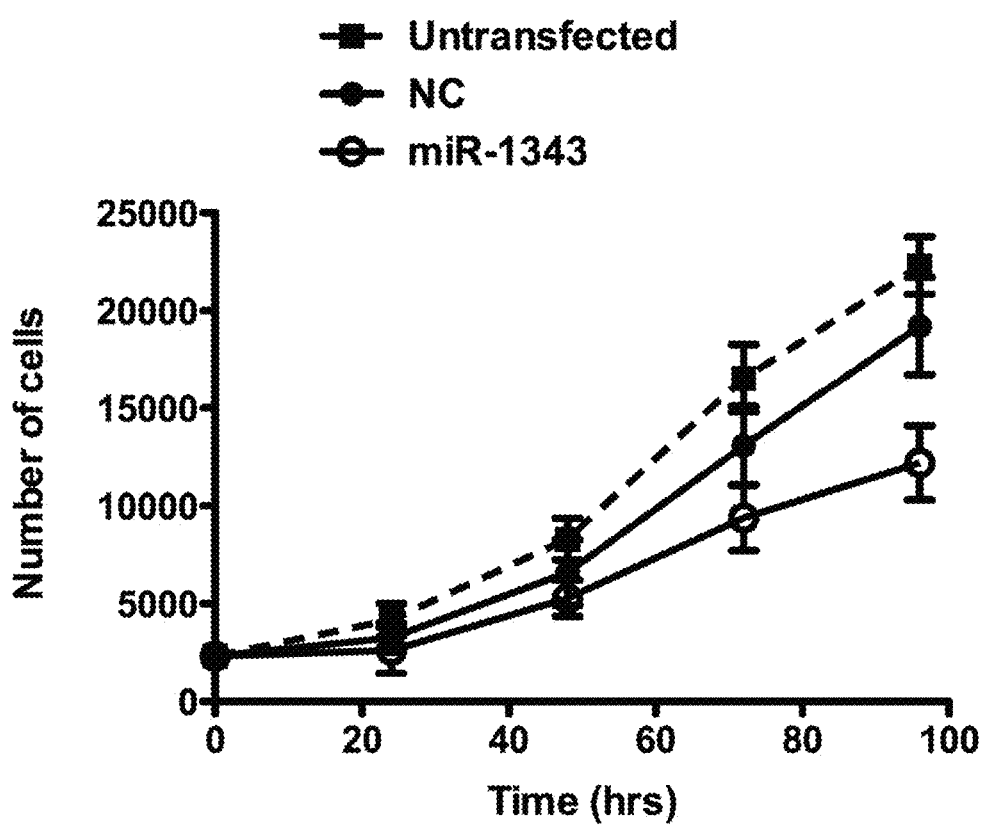
FIG. 14: Growth curve of A549 cells transiently transfected with pre-miR-1343 or negative control (NC) miRNA by MTS assay.

Simultaneously, a scratch wound was made across the confluent A549 cell monolayer and movement into the wound was monitored microscopically during the following 24 hours (FIG. 5d,e). NC-treated cells exhibited marked wound closure in the presence of TGF-β, with the wound area closing 60% from an average of 0.60 $mm^2$ to 0.24 $mm^2$. However, wound healing into the scratch was considerably reduced in miR-1343 treated cells, with wound area closing only 40% from 0.6 $mm^2$ to 0.36 $mm^2$. Pre-miR-1343 transfected into A549 cells was also shown to slightly impair cell proliferation compared to NC transfected cells FIG. 14). These results indicate that miR-1343 reduces cell migration into a wound.

Figure 6A:
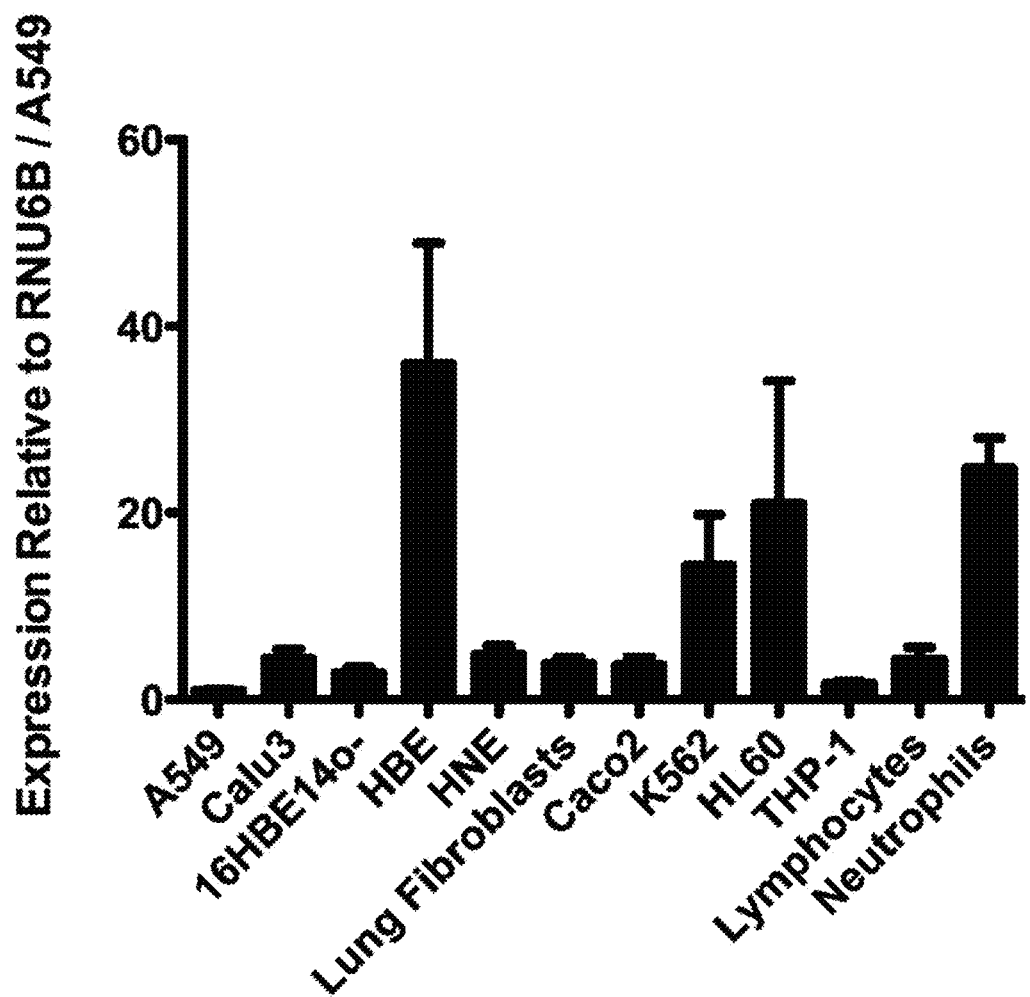
FIGS. 6A-C: Mature miR-1343 expression is most abundant in neutrophils and is induced by serum starvation in lung epithelial cells. (A) miR-1343 expression levels measured by TaqMan RT-qPCR assay across various cell types. Values are normalized to RNU6B and are shown relative to A549 levels. A549, Calu3, 16HBE14o-, HBE (primary human bronchial epithelial cells), HNE (human nasal epithelial cells), primary lung fibroblasts, Caco2, K562, HL-60, THP-1, primary lymphocytes, and primary neutrophils are shown. (B) Northern blot showing levels of miR-1343 in various lung cell types. Black arrows indicate unprocessed (~85 bp), precursor (~60 bp), and mature (~23 bp) miRNA forms. Blots were stripped and re-hybridized with a probe against U6 small nuclear RNA to confirm equal loading. A549, A549 serum starved cells, A549 cells treated with TGF-β$_1$ (5 ng/mL) in serum-depleted media for 48 hours, Calu3, 16HBE14o-, and primary lung fibroblast RNA are shown. (C) Northern blot showing levels of miR-1343 in various hematopoietic cell types. Black arrows indicate unprocessed (~85 bp), precursor (~60 bp), and mature (~23 bp) miRNA forms. Blots were stripped and re-hybridized with a probe against U6 small nuclear RNA to confirm equal loading. Primary human neutrophils, K562, HL-60, and THP-1 RNA are shown.

Example 7 miR-1343 is Processed in Hematopoietic Cells and in Airway Epithelial Cells Under Stress Observations on the effects of miR-1343 on the TGF-β signaling pathway in lung epithelial cells and fibroblasts primarily used exogenous precursor-miRNA transfected into cells. The abundance and maturation of endogenous miR-1343 was examined in primary cells with an important role in lung biology and relevant derivative cell lines. First, a commercial RT-qPCR TaqMan assay (Life Technologies) was used, which is designed to detect only mature miR-1343, with levels normalized to the small nuclear RNA (RNU6B). miR-1343 levels were assayed in A549 and Calu3 lung adenocarcinoma cells, 16HBE14o-, primary human bronchial epithelial cells (HBE), human nasal epithelial cells (HNE, from nasal scrapes), primary lung fibroblasts, Caco2, HL-60 promyelocytic leukemia cells, K562 erythroleukemia cells, THP-1 acute monocytic leukemia cells, primary human lymphocytes, and primary human neutrophils (FIG. 6a). Expression levels of miR-1343 were similar in all cell types assayed with the exception of primary HBE cells, neutrophils, and the HL-60 and K562 cell lines, which had ~20 to 40 fold more miRNA than the lowest-expressing A549 cells.

Figure 6B:
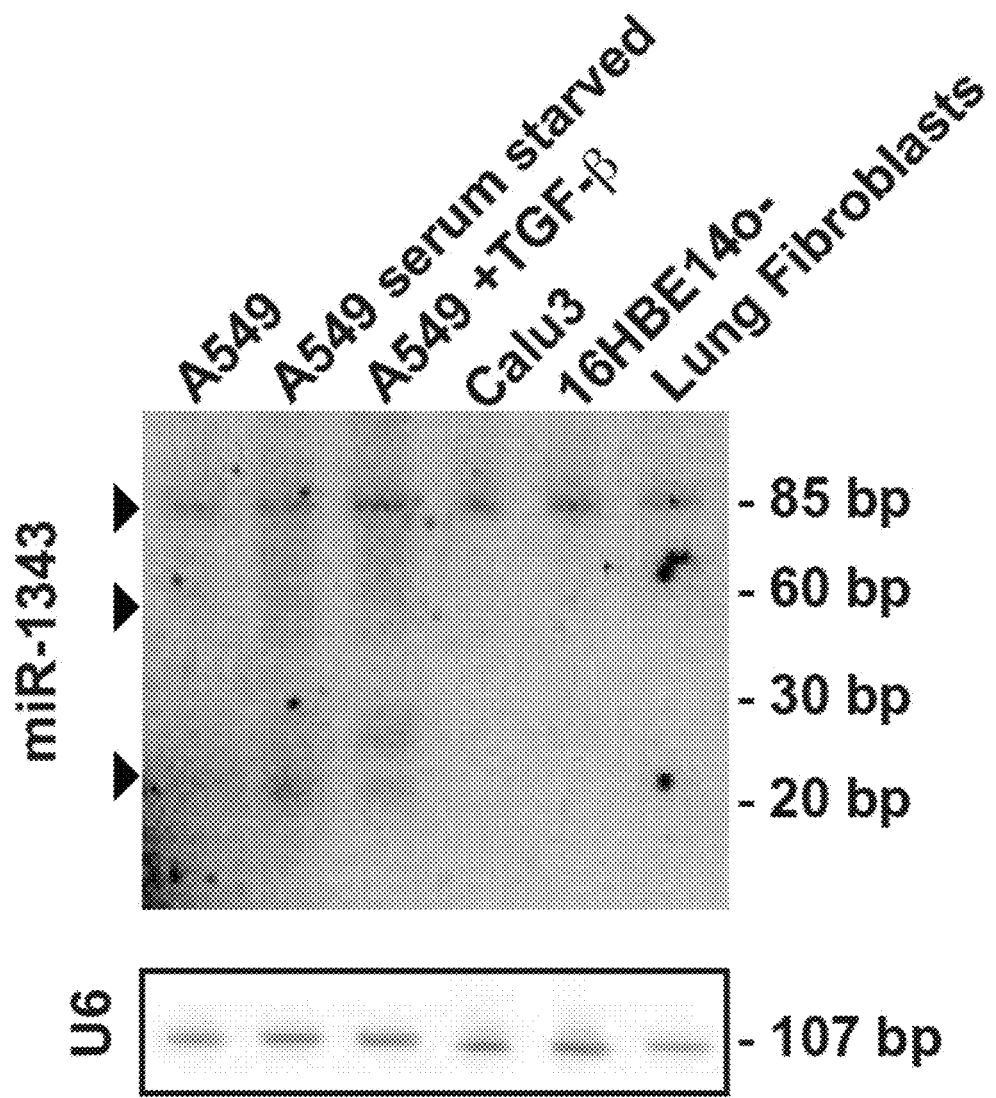

To directly measure endogenous levels of miR-1343 and to distinguish between the precursor and mature forms of the miRNA, northern blots of RNA extracted were performed from the same cell types (FIG. 6b,c). Northern blots were probed with $^{32}$P-labelled DNA probes complementary to human miR-1343-3p, and U6 small nuclear RNA as a loading control. An unprocessed transcript (~85 bp) was equally abundant in all cell types. However, processed forms of miR-1343 (premature ~60 bp, mature ~23 bp), were only detected in primary neutrophils and HL-60 cells, and in A549 cells that were serum starved and/or treated with TGF-β for a period of 48 hours (FIG. 6b,c). These results indicate that the main source of processed miR-1343 under normal conditions is within neutrophils and that it can be induced in lung epithelial cells upon stress.

Example 8

Figure 6C:
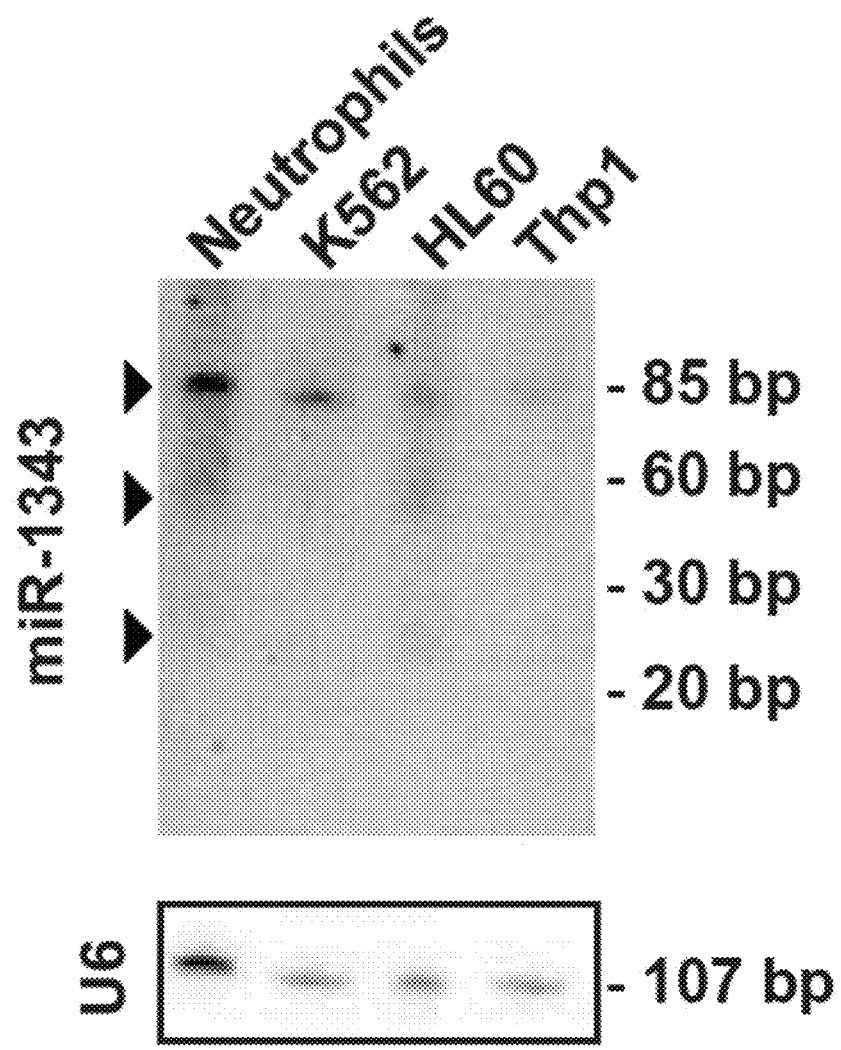
Figure 15A:
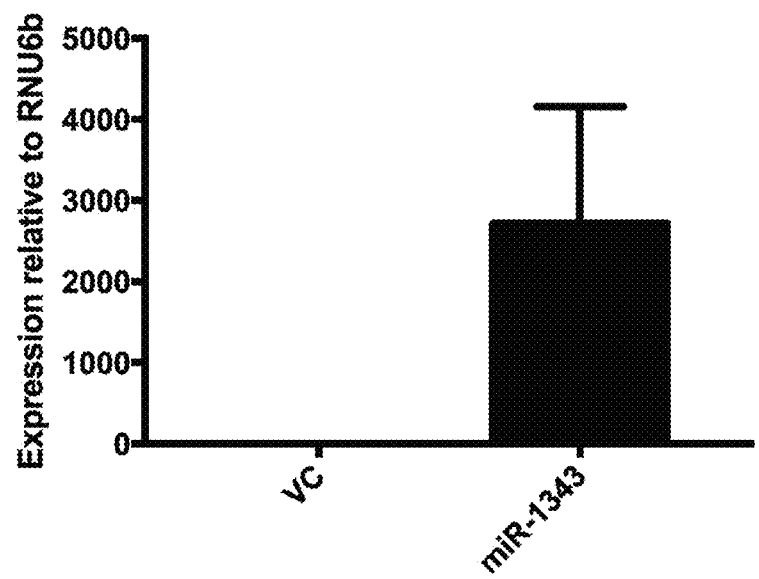
FIG. 15A-B: miR-1343 is highly synthesized in HL-60 cells and can be transferred to A549 cells. (A) miR-1343 expression as measured by TaqMan qRT-PCR assay in HL-60 cells following electroporation with pCMV-MIR (vector control, VC) or pCMV-MIR-1343 (miR-1343) vectors for 48 hrs. Levels of miR-1343 were normalized to RNU6b and shown relative to VC. (B) miR-1343 expression measured in A549 cells conditioned with media from HL-60 cells in (A) for 48 hrs. Levels of miR-1343 were normalized to RNU6b and shown relative to VC.

Experiments conducted during development of embodiments herein demonstrate that miR-1343 is transferred between cells in culture via exosomes. Data indicated that miR-1343 was highly expressed in human neutrophils (FIG. 6). In further experiments, miR-1343 was overexpressed in the HL-60 neutrophil-like cell line using the pCMV-MIR vector (Origene). pCMV-MIR (empty vector control) or pCMV-MIR-1343, wherein a ~300 bp sequence containing miR-1343 was cloned downstream of the cytomegalovirus (CMV) promoter, were electroporated into HL-60 cells for 48 hours. Cells were then lysed and miR-1343 expression was measured by a TaqMan quantitative RT-PCR assay specific for mature miR-1343. FIG. 15A shows that miR-1343 levels in HL-60 cells exceeded 2000 fold compared to the vector control, demonstrating efficient expression of miR-1343 in the HL-60 cells.

Figure 15B:
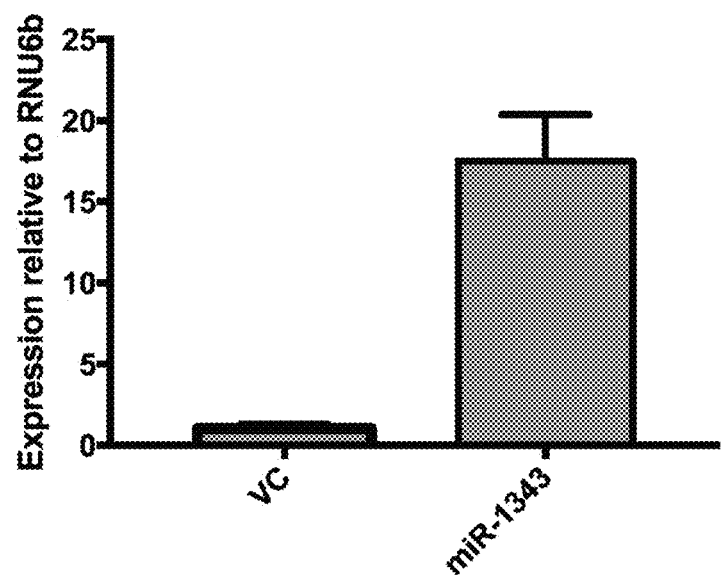

Experiments were conducted during development of embodiments herein to determine whether miR-1343 from over-expressing HL-60 cells is transferred to A549 lung epithelial cells. HL-60 cells were electroporated with pCMV-MIR or pCMV-MIR-1343 as above and were allowed to condition their media for 48 hours. The conditioned media was then transferred to A549 cells for 48 hours and miR-1343 expression was measured by TaqMan assay as above (FIG. 15B). It was found that these conditioned A549 cells exhibited approximately 17-fold more miR-1343 compared to the vector control cells, demonstrating that miR-1343 is transferred between cell types.

Figure 16A:
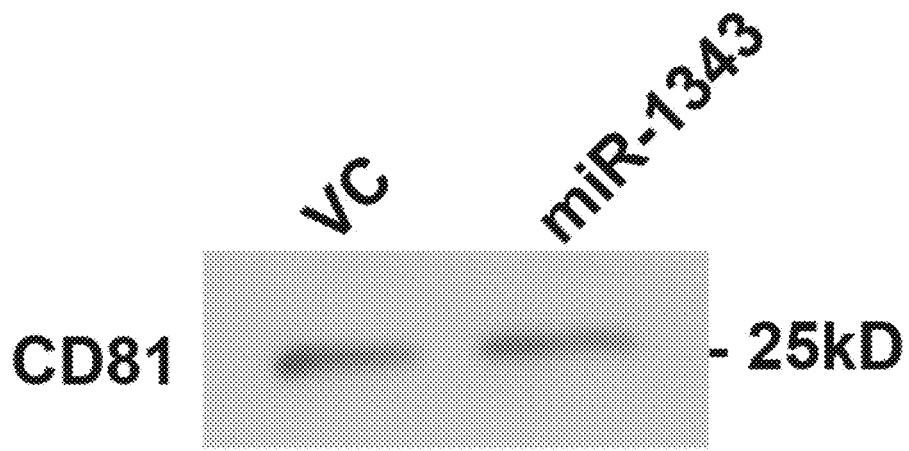
FIG. 16A-C: miR-1343 from HL-60 cells is contained within exosomes. HL-60 cells were electroporated with pCMV-MIR (vector control, VC) or pCMV-MIR-1343 (miR-1343) vectors and conditioned in exosome-free media for 48 hours. Exosomes were purified via ultracentrifugation and lysed. (A) Exosome lysates were separated via SDS-PAGE and probed with an antibody specific for exosomal marker CD81. (B) Levels of miR-1343 measured by TaqMan qRT-PCR assay from HL-60 cells and exosome lysates. Values were normalized against a standard curve and represented relative to VC. (C) Purified exosomes were serially diluted and incubated with A549 cells for 48 hours. miR-1343 levels were measured by TaqMan qRT-PCR assay and normalized against RNU6b relative to VC.
Figure 16B:
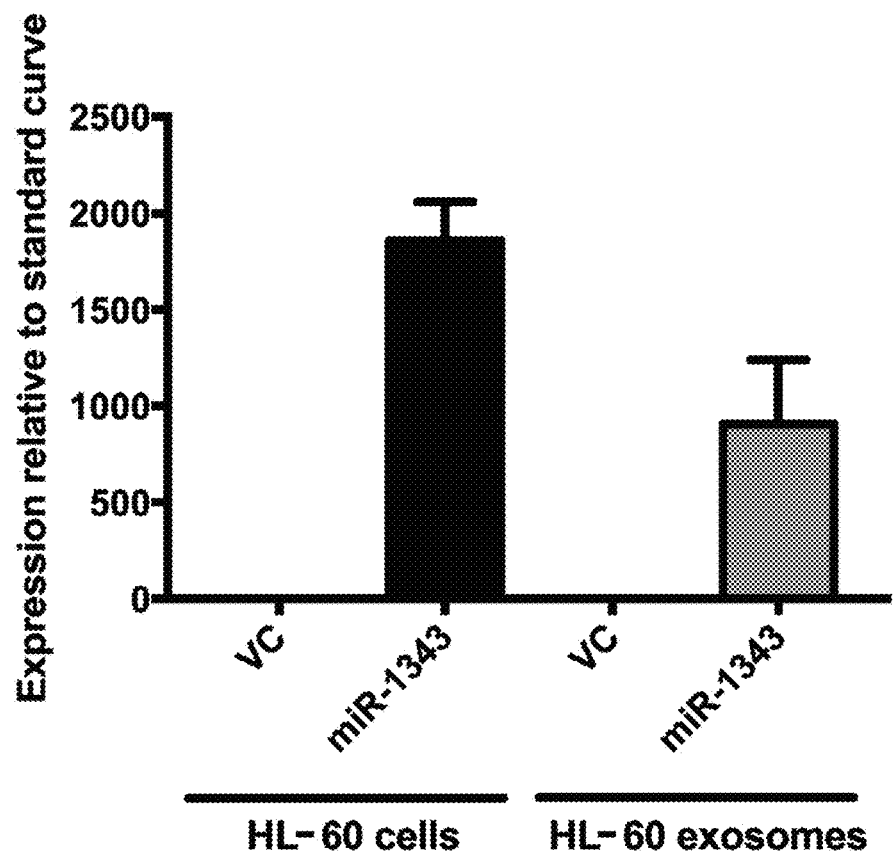

To elucidate the mechanism by which miR-1343 is trafficked between cells, HL-60 cells were electroporated with pCMV-MIR or pCMV-MIR-1343 vectors as above and allowed to grow in exosome-depleted media for 48 hours. Following the incubation, exosomes were purified via ultracentrifugation methods. Exosome lysates were run on non-reducing SDS-PAGE and probed with an antibody specific for a marker of exosomes, CD81. FIG. 16A shows abundant CD81 from both vector control and miR-1343 over-expressing cells, demonstrating successful isolation of exosomes. Furthermore, RNA was extracted from the exosome lysates, along with the donating HL-60 cells, and miR-1343 expression was measured by TaqMan assay (FIG. 16B). Exosomes purified from miR-1343 over-expressing HL-60 cells contained significantly more miR-1343 compared to exosomes from vector control cells. Levels of miR-1343 in exosomes were similar to those expressed within the HL-60 cells themselves.

Figure 16C:
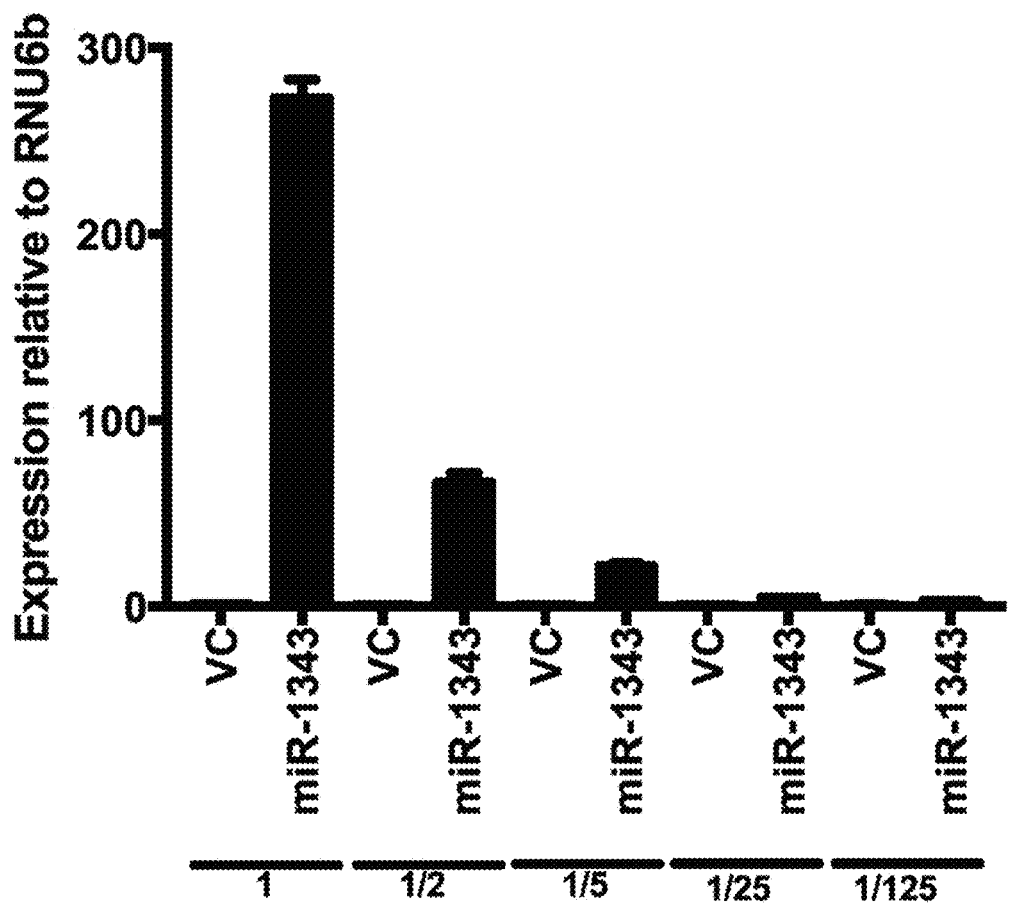

To demonstrate miR-1343-containing exosomes being taken up by recipient cells, exosomes were purified as above and directly used to treat A549 cells. Exosomes were serially diluted and incubated with A549 cells in exosome-free media for 48 hours. RNA was isolated from the cells and a TaqMan assay was used to measure miR-1343 expression within them (FIG. 16C). miR-1343 was expressed at levels strongly correlated with exosome dose, with the highest dose showing ~275-fold miR-1343 over-expression compared to the vector control. This demonstrates that miR-1343 is transferred between cell types via exosome secretion and subsequent uptake.

These results highlight a signaling role for miR-1343 and indicate a mechanism for the treatment for fibrosis.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

REFERENCES

The following references, some of which are cited above by number, are herein incorporated by reference in their entireties.

1 Rackley, C. R. and Stripp, B. R. (2012) Building and maintaining the epithelium of the lung. J. Clin. Invest. 122, 2724-30.
2 Wynn, T. A. (2011) Integrating mechanisms of pulmonary fibrosis. J. Exp. Med. 208, 1339-50.
3 Leask, A. and Abraham, D. J. (2004) TGF-beta signaling and the fibrotic response. FASEB J. 18, 816-27.
4 Mak, J. C. W., Chan-Yeung, M. M. W., Ho, S. P., Chan, K. S., Choo, K., Yee, K. S., Chau, C. H., Cheung, A. H. K. and Ip, M. S. M. (2009) Elevated plasma TGF-beta1 levels in patients with chronic obstructive pulmonary disease. Respir. Med. 103, 1083-9.
5 Harris, W. T., Muhlebach, M. S., Oster, R. A., Knowles, M. R. and Noah, T. L. (2009) Transforming growth factor-beta(1) in bronchoalveolar lavage fluid from children with cystic fibrosis. Pediatr. Pulmonol. 44, 1057-64.
6 Santana, A., Saxena, B., Noble, N. A., Gold, L. I. and Marshall, B. C. (1995) Increased expression of transforming growth factor beta isoforms (beta 1, beta 2, beta 3) in bleomycin-induced pulmonary fibrosis. Am. J. Respir. Cell Mol. Biol. 13, 34-44.
7 Roberts, A. B., Sporn, M. B., Assoian, R. K., Smith, J. M., Roche, N. S., Wakefield, L. M., Heine, U. I., Liotta, L. A., Falanga, V. and Kehrl, J. H. (1986) Transforming growth factor type beta: rapid induction of fibrosis and angiogenesis in vivo and stimulation of collagen formation in vitro. Proc. Natl. Acad. Sci. U.S.A 83, 4167-71.
8 Willis, B. C., Liebler, J. M., Luby-Phelps, K., Nicholson, A. G., Crandall, E. D., du Bois, R. M. and Borok, Z. (2005) Induction of epithelial-mesenchymal transition in alveolar epithelial cells by transforming growth factor-beta1: potential role in idiopathic pulmonary fibrosis. Am. J. Pathol. 166, 1321-32.
9 Vanscoy, L. L., Blackman, S. M., Collaco, J. M., Bowers, A., Lai, T., Naughton, K., Algire, M., McWilliams, R., Beck, S., Hoover-Fong, J., et al. (2007) Heritability of lung disease severity in cystic fibrosis. Am. J. Respir. Crit. Care Med. 175, 1036-43.
10 Scholand, M. B., Coon, H., Wolff, R. and Cannon-Albright, L. (2013) Use of a genealogical database demonstrates heritability of pulmonary fibrosis. Lung 191, 475-81.
11 Silverman, E. K., Pierce, J. A., Province, M. A., Rao, D. C. and Campbell, E. J. (1989) Variability of pulmonary function in alpha-1-antitrypsin deficiency: clinical correlates. Ann. Intern. Med. 111, 982-91.
12 Celedón, J. C., Lange, C., Raby, B. A., Litonjua, A. A., Palmer, L. J., DeMeo, D. L., Reilly, J. J., Kwiatkowski, D. J., Chapman, H. A., Laird, N., et al. (2004) The transforming growth factor-beta1 (TGFB1) gene is associated with chronic obstructive pulmonary disease (COPD). Hum. Mol. Genet. 13, 1649-56.
13 Wu, L., Chau, J., Young, R. P., Pokorny, V., Mills, G. D., Hopkins, R., McLean, L. and Black, P. N. (2004) Transforming growth factor-beta1 genotype and susceptibility to chronic obstructive pulmonary disease. Thorax 59, 126-9.
14 Drumm, M. L., Konstan, M. W., Schluchter, M. D., Handler, A., Pace, R., Zou, F., Zariwala, M., Fargo, D., Xu, A., Dunn, J. M., et al. (2005) Genetic modifiers of lung disease in cystic fibrosis. N. Engl. J. Med. 353, 1443-53.
15 Arkwright, P. D., Laurie, S., Super, M., Pravica, V., Schwarz, M. J., Webb, A. K. and Hutchinson, I. V. (2000) TGF-beta(1) genotype and accelerated decline in lung function of patients with cystic fibrosis. Thorax 55, 459-62.
16 Lu, J., Getz, G., Miska, E. A., Alvarez-Saavedra, E., Lamb, J., Peck, D., Sweet-Cordero, A., Ebert, B. L., Mak, R. H., Ferrando, A. A., et al. (2005) MicroRNA expression profiles classify human cancers. Nature 435, 834-8.
17 Jiang, Q., Wang, Y., Hao, Y., Juan, L., Teng, M., Zhang, X., Li, M., Wang, G. and Liu, Y. (2009) miR2Disease: a 18 Pandit, K. V, Corcoran, D., Yousef, H., Yarlagadda, M., Tzouvelekis, A., Gibson, K. F., Konishi, K., Yousem, S. A., Singh, M., Handley, D., et al. (2010) Inhibition and role of let-7d in idiopathic pulmonary fibrosis. Am. J. Respir. Crit. Care Med. 182, 220-9.

19 Pottier, N., Maurin, T., Chevalier, B., Puisségur, M.-P., Lebrigand, K., Robbe-Sermesant, K., Bertero, T., Lino Cardenas, C. L., Courcot, E., Rios, G., et al. (2009) Identification of keratinocyte growth factor as a target of microRNA-155 in lung fibroblasts: implication in epithelial-mesenchymal interactions. PLoS One 4, e6718.

20 Bhattacharyya, S., Balakathiresan, N. S., Dalgard, C., Gutti, U., Armistead, D., Jozwik, C., Srivastava, M., Pollard, H. B. and Biswas, R. (2011) Elevated miR-155 promotes inflammation in cystic fibrosis by driving hyperexpression of interleukin-8. J. Biol. Chem. 286, 11604-15.

21 Yang, S., Cui, H., Xie, N., Icyuz, M., Banerjee, S., Antony, V. B., Abraham, E., Thannickal, V. J. and Liu, G. (2013) miR-145 regulates myofibroblast differentiation and lung fibrosis. FASEB J. 27, 2382-91.

22 Liu, G., Friggeri, A., Yang, Y., Milosevic, J., Ding, Q., Thannickal, V. J., Kaminski, N. and Abraham, E. (2010) miR-21 mediates fibrogenic activation of pulmonary fibroblasts and lung fibrosis. J. Exp. Med. 207, 1589-97.

23 Megiorni, F., Cialfi, S., Cimino, G., De Biase, R. V., Dominici, C., Quattrucci, S. and Pizzuti, A. (2013) Elevated levels of miR-145 correlate with SMAD3 down-regulation in cystic fibrosis patients. J. Cyst. Fibros. 12, 797-802.

24 Xiao, J., Meng, X.-M., Huang, X. R., Chung, A. C., Feng, Y.-L., Hui, D. S., Yu, C.-M., Sung, J. J. and Lan, H. Y. (2012) miR-29 inhibits bleomycin-induced pulmonary fibrosis in mice. Mol. Ther., The American Society of Gene & Cell Therapy 20, 1251-60.

25 Montgomery, R. L., Yu, G., Latimer, P. A., Stack, C., Robinson, K., Dalby, C. M., Kaminski, N. and van Rooij, E. (2014) MicroRNA mimicry blocks pulmonary fibrosis. EMBO Mol. Med. 6, 1347-56.

26 Yang, S., Xie, N., Cui, H., Banerjee, S., Abraham, E., Thannickal, V. J. and Liu, G. (2012) miR-31 is a negative regulator of fibrogenesis and pulmonary fibrosis. FASEB J. 26, 3790-9.

27 Meunier, J., Lemoine, F., Soumillon, M., Liechti, A., Weier, M., Guschanski, K., Hu, H., Khaitovich, P. and Kaessmann, H. (2013) Birth and expression evolution of mammalian microRNA genes. Genome Res. 23, 34-45.

28 Persson, H., Kvist, A., Rego, N., Staaf, J., Vallon-Christersson, J., Luts, L., Loman, N., Jonsson, G., Naya, H., Hoglund, M., et al. (2011) Identification of new microRNAs in paired normal and tumor breast tissue suggests a dual role for the ERBB2/Her2 gene. Cancer Res. 71, 78-86.

29 Glazov, E. A., Kongsuwan, K., Assavalapsakul, W., Horwood, P. F., Mitter, N. and Mahony, T. J. (2009) Repertoire of bovine miRNA and miRNA-like small regulatory RNAs expressed upon viral infection. PLoS One 4, e6349.

30 Chen, C., Deng, B., Qiao, M., Zheng, R., Chai, J., Ding, Y., Peng, J. and Jiang, S. (2012) Solexa sequencing identification of conserved and novel microRNAs in backfat of Large White and Chinese Meishan pigs. PLoS One 7, e31426.

31 Dannemann, M., Nickel, B., Lizano, E., Burbano, H. A. and Kelso, J. (2012) Annotation of primate miRNAs by high throughput sequencing of small RNA libraries. BMC Genomics 13, 116.

32 Wright, F. A., Strug, L. J., Doshi, V. K., Commander, C. W., Blackman, S. M., Sun, L., Berthiaume, Y., Cutler, D., Cojocaru, A., Collaco, J. M., et al. (2011) Genome-wide association and linkage identify modifier loci of lung disease severity in cystic fibrosis at 11p13 and 20q13.2. Nat. Genet. 43, 539-46.

33 Giard, D. J., Aaronson, S. A., Todaro, G. J., Arnstein, P., Kersey, J. H., Dosik, H. and Parks, W. P. (1973) In vitro cultivation of human tumors: establishment of cell lines derived from a series of solid tumors. J. Natl. Cancer Inst. 51, 1417-23.

34 Cozens, A. L., Yezzi, M. J., Kunzelmann, K., Ohrui, T., Chin, L., Eng, K., Finkbeiner, W. E., Widdicombe, J. H. and Gruenert, D. C. (1994) CFTR expression and chloride secretion in polarized immortal human bronchial epithelial cells. Am. J. Respir. Cell Mol. Biol. 10, 38-47.

35 Fogh, J., Fogh, J. M. and Orfeo, T. (1977) One hundred and twenty-seven cultured human tumor cell lines producing tumors in nude mice. J. Natl. Cancer Inst. 59, 221-6.

36 Gillen, A. E., Gosalia, N., Leir, S.-H. and Harris, A. (2011) MicroRNA regulation of expression of the cystic fibrosis transmembrane conductance regulator gene. Biochem. J. 438, 25-32.

37 Wrana, J. L., Attisano, L., Cárcamo, J., Zentella, A., Doody, J., Laiho, M., Wang, X. F. and Massagué, J. (1992) TGF beta signals through a heteromeric protein kinase receptor complex. Cell 71, 1003-14.

38 Fossum, S. L., Mutolo, M. J., Yang, R., Dang, H., O'Neal, W. K., Knowles, M. R., Leir, S.-H. and Harris, A. (2014) Ets homologous factor regulates pathways controlling response to injury in airway epithelial cells. Nucleic Acids Res. 42, 13588-98.

39 Leir, S.-H., Holgate, S. T. and Lackie, P. M. (2003) Inflammatory cytokines can enhance CD44-mediated airway epithelial cell adhesion independently of CD44 expression. Am. J. Physiol. Lung Cell. Mol. Physiol. 285, L1305-11.

40 Alexiou, P., Maragkakis, M., Papadopoulos, G. L., Reczko, M. and Hatzigeorgiou, A. G. (2009) Lost in translation: an assessment and perspective for computational microRNA target identification. Bioinformatics 25, 3049-55.

41 Lewis, B. P., Burge, C. B. and Bartel, D. P. (2005) Conserved seed pairing, often flanked by adenosines, indicates that thousands of human genes are microRNA targets. Cell 120, 15-20.

42 Trapnell, C., Roberts, A., Goff, L., Pertea, G., Kim, D., Kelley, D. R., Pimentel, H., Salzberg, S. L., Rinn, J. L. and Pachter, L. (2012) Differential gene and transcript expression analysis of RNA-seq experiments with TopHat and Cufflinks. Nat. Protoc. 7, 562-78.

43 Huang, D. W., Sherman, B. T. and Lempicki, R. A. (2009) Systematic and integrative analysis of large gene lists using DAVID bioinformatics resources. Nat. Protoc. 4, 44-57.

44 Huang, D. W., Sherman, B. T. and Lempicki, R. A. (2009) Bioinformatics enrichment tools: paths toward the comprehensive functional analysis of large gene lists. Nucleic Acids Res. 37, 1-13.

45 Shi, Y. and Massagué, J. (2003) Mechanisms of TGF-beta signaling from cell membrane to the nucleus. Cell 113, 685-700.

46 Leask, A. and Abraham, D. J. (2004) TGF-beta signaling and the fibrotic response. FASEB J. 18, 816-27.
47 Kasai, H., Allen, J. T., Mason, R. M., Kamimura, T. and Zhang, Z. (2005) TGF-beta1 induces human alveolar epithelial to mesenchymal cell transition (EMT). Respir. Res. 6, 56.
48 Dorfman, R., Sandford, A., Taylor, C., Huang, B., Frangolias, D., Wang, Y., Sang, R., Pereira, L., Sun, L., Berthiaume, Y., et al. (2008) Complex two-gene modulation of lung disease severity in children with cystic fibrosis. J. Clin. Invest. 118, 1040-9.
49 Lagraoui, M. and Gagnon, L. (1997) Enhancement of human neutrophil survival and activation by TGF-beta 1. Cell. Mol. Biol. (Noisy-le-grand). 43, 313-8.
50 Feng, D.-Q., Huang, B., Li, J., Liu, J., Chen, X.-M., Xu, Y.-M., Chen, X., Zhang, H.-B., Hu, L.-H. and Wang, X.-Z. (2013) Selective miRNA expression profile in chronic myeloid leukemia K562 cell-derived exosomes. Asian Pac. J. Cancer Prev. 14, 7501-8.
51 Huan, J., Hornick, N. I., Shurtleff, M. J., Skinner, A. M., Goloviznina, N. A., Roberts, C. T. and Kurre, P. (2013) RNA trafficking by acute myelogenous leukemia exosomes. Cancer Res. 73, 918-29.
52 Pirkmajer, S. and Chibalin, A. V. (2011) Serum starvation: caveat emptor. Am. J. Physiol. Cell Physiol. 301, C272-9.
53 Li, G., Luna, C., Qiu, J., Epstein, D. L. and Gonzalez, P. Alterations in microRNA expression in stress-induced cellular senescence. Mech. Ageing Dev. 130, 731-41.
54 Suzuki, H. I., Yamagata, K., Sugimoto, K., Iwamoto, T., Kato, S. and Miyazono, K. (2009) Modulation of microRNA processing by p53. Nature, Macmillan Publishers Limited. All rights reserved 460, 529-33.
55 Simone, N. L., Soule, B. P., Ly, D., Saleh, A. D., Savage, J. E., Degraff, W., Cook, J., Harris, C. C., Gius, D. and Mitchell, J. B. (2009) Ionizing radiation-induced oxidative stress alters miRNA expression. PLoS One, Public Library of Science 4, e6377.
56 Bhattacharyya, S. N., Habermacher, R., Martine, U., Closs, E. I. and Filipowicz, W. (2006) Relief of microRNA-mediated translational repression in human cells subjected to stress. Cell 125, 1111-24.
57 Leung, A. K. L., Calabrese, J. M. and Sharp, P. A. (2006) Quantitative analysis of Argonaute protein reveals microRNA-dependent localization to stress granules. Proc. Natl. Acad. Sci. U.S.A 103, 18125-30.
58 Piriyapongsa, J., Mariño-Ramírez, L. and Jordan, I. K. (2007) Origin and evolution of human microRNAs from transposable elements. Genetics 176, 1323-37.
59 Kozomara, A. and Griffiths-Jones, S. (2014) miRBase: annotating high confidence microRNAs using deep sequencing data. Nucleic Acids Res. 42, D68-73.
60 Altschul, S. F., Gish, W., Miller, W., Myers, E. W. and Lipman, D. J. (1990) Basic local alignment search tool. J. Mol. Biol. 215, 403-10.
61 Friedman, S. L., Sheppard, D., Duffield, J. S. and Violette, S. (2013) Therapy for fibrotic diseases: nearing the starting line. Sci. Transl. Med. 5, 167sr1.
62 Li, Z. and Rana, T. M. (2014) Therapeutic targeting of microRNAs: current status and future challenges. Nat. Rev. Drug Discov., Nature Publishing Group 13, 622-638.
63 Bader, A. G., Brown, D. and Winkler, M. (2010) The promise of microRNA replacement therapy. Cancer Res. 70, 7027-30.
64 Takeshita, F., Patrawala, L., Osaki, M., Takahashi, R., Yamamoto, Y., Kosaka, N., Kawamata, M., Kelnar, K., Bader, A. G., Brown, D., et al. (2010) Systemic delivery of synthetic microRNA-16 inhibits the growth of metastatic prostate tumors via downregulation of multiple cell-cycle genes. Mol. Ther. 18, 181-7.
65 Wiggins, J. F., Ruffino, L., Kelnar, K., Omotola, M., Patrawala, L., Brown, D. and Bader, A. G. (2010) Development of a lung cancer therapeutic based on the tumor suppressor microRNA-34. Cancer Res. 70, 5923-30.

SEQUENCES

SEQ ID NO: 43
CUCCUGGGGCCCGCACUCUCGC

The invention claimed is:

1. A method of treating or preventing fibrosis in a subject comprising administering a pharmaceutical composition comprising a miR-1343 molecule to the subject, wherein the miR-1343 molecule is miR-1343 (SEQ ID NO:43) or a variant thereof that has at least 70% sequence identity to the complete length of SEQ ID NO: 43 and that inhibits expression of TGFβRI and/or TGFβR2.

2. The method of claim 1, wherein the subject suffers from a pulmonary form of fibrosis.

3. The method of claim 2, wherein the subject suffers from idiopathic pulmonary fibrosis, chronic obstructive pulmonary disease, and/or cystic fibrosis.

4. The method of claim 1, wherein the miR-1343 molecule is vesicle formulated.

5. The method of claim 1, wherein the miR-1343 molecule is administered by inhalation, topically, transdermally, or by injection.

6. The method of claim 1, wherein the miR-1343 molecule is administered to epithelial cells of the subject.

7. The method of claim 6, wherein the miR-1343 molecule is administered directly to the epithelial cells.

8. The method of claim 6, wherein the miR-1343 molecule is administered systemically and localizes in the epithelial cells.

9. The method of claim 6, wherein the miR-1343 molecule is administered to pulmonary epithelial cells.

* * * * *

SEQUENCE LISTING

<160> NUMBER OF SEQ ID NOS: 43

<210> SEQ ID NO 1
<211> LENGTH: 32
<212> TYPE: DNA
<213> ORGANISM: Artificial sequence
<220> FEATURE:
<223> OTHER INFORMATION: DNA Primer

<400> SEQUENCE: 1
ggactagttt ctacagcttt gcctgaactc tc                                    32

<210> SEQ ID NO 2
<211> LENGTH: 28
<212> TYPE: DNA
<213> ORGANISM: Artificial sequence
<220> FEATURE:
<223> OTHER INFORMATION: DNA Primer

<400> SEQUENCE: 2
cgacgcgtcc ttcgccttcc tagaaaaa                                        28

<210> SEQ ID NO 3

```
<211> LENGTH: 20
<212> TYPE: DNA
<213> ORGANISM: Artificial sequence
<220> FEATURE:
<223> OTHER INFORMATION: DNA Primer

<400> SEQUENCE: 3
ctgcccctga actgatgctt                                              20

<210> SEQ ID NO 4
<211> LENGTH: 20
<212> TYPE: DNA
<213> ORGANISM: Artificial sequence
<220> FEATURE:
<223> OTHER INFORMATION: DNA Primer

<400> SEQUENCE: 4
ggtccaggta ggcagtggaa                                              20

<210> SEQ ID NO 5
<211> LENGTH: 18
<212> TYPE: DNA
<213> ORGANISM: Artificial sequence
<220> FEATURE:
<223> OTHER INFORMATION: DNA Primer

<400> SEQUENCE: 5
cctggagcca gaaacgac                                                18

<210> SEQ ID NO 6
<211> LENGTH: 20
<212> TYPE: DNA
<213> ORGANISM: Artificial sequence
<220> FEATURE:
<223> OTHER INFORMATION: DNA Primer

<400> SEQUENCE: 6
catggttact gacaggaagc                                              20

<210> SEQ ID NO 7
<211> LENGTH: 26
<212> TYPE: DNA
<213> ORGANISM: Artificial sequence
<220> FEATURE:
<223> OTHER INFORMATION: DNA Primer

<400> SEQUENCE: 7
actagtgcat tgatactgct ggcacc                                       26

<210> SEQ ID NO 8
<211> LENGTH: 27
<212> TYPE: DNA
<213> ORGANISM: Artificial sequence
<220> FEATURE:
<223> OTHER INFORMATION: DNA Primer

<400> SEQUENCE: 8
gagctcgcac aaagtctgga agcaagc                                      27

<210> SEQ ID NO 9
<211> LENGTH: 25
<212> TYPE: DNA
<213> ORGANISM: Artificial sequence
<220> FEATURE:
<223> OTHER INFORMATION: DNA Primer

<400> SEQUENCE: 9
```

-continued

```
actagttctg ttgcccaacc tggag                                    25

<210> SEQ ID NO 10
<211> LENGTH: 27
<212> TYPE: DNA
<213> ORGANISM: Artificial sequence
<220> FEATURE:
<223> OTHER INFORMATION: DNA Primer

<400> SEQUENCE: 10
gagctcgaga tcacctgtgg gtcaagg                                  27

<210> SEQ ID NO 11
<211> LENGTH: 27
<212> TYPE: DNA
<213> ORGANISM: Artificial sequence
<220> FEATURE:
<223> OTHER INFORMATION: DNA Primer

<400> SEQUENCE: 11
cctagggcaa ccaaaggcaa cagagtc                                  27

<210> SEQ ID NO 12
<211> LENGTH: 29
<212> TYPE: DNA
<213> ORGANISM: Artificial sequence
<220> FEATURE:
<223> OTHER INFORMATION: DNA Primer

<400> SEQUENCE: 12
ggcgcgccca cataggaaca ttggcctgc                                29

<210> SEQ ID NO 13
<211> LENGTH: 26
<212> TYPE: DNA
<213> ORGANISM: Artificial sequence
<220> FEATURE:
<223> OTHER INFORMATION: DNA Primer

<400> SEQUENCE: 13
cctagggcct tgtcatcggt tgtgtg                                   26

<210> SEQ ID NO 14
<211> LENGTH: 29
<212> TYPE: DNA
<213> ORGANISM: Artificial sequence
<220> FEATURE:
<223> OTHER INFORMATION: DNA Primer

<400> SEQUENCE: 14
ggcgcgccct gctgcctaca cacttcctt                                29

<210> SEQ ID NO 15
<211> LENGTH: 20
<212> TYPE: DNA
<213> ORGANISM: Artificial sequence
<220> FEATURE:
<223> OTHER INFORMATION: DNA Primer

<400> SEQUENCE: 15
cggggagaag aagttgctgt                                          20

<210> SEQ ID NO 16
<211> LENGTH: 20
<212> TYPE: DNA
```

```
<213> ORGANISM: Artificial sequence
<220> FEATURE:
<223> OTHER INFORMATION: DNA Primer

<400> SEQUENCE: 16
caccaaccag agctgagtcc                                                    20

<210> SEQ ID NO 17
<211> LENGTH: 21
<212> TYPE: DNA
<213> ORGANISM: Artificial sequence
<220> FEATURE:
<223> OTHER INFORMATION: DNA Primer

<400> SEQUENCE: 17
aataggactg cccatccact g                                                  21

<210> SEQ ID NO 18
<211> LENGTH: 21
<212> TYPE: DNA
<213> ORGANISM: Artificial sequence
<220> FEATURE:
<223> OTHER INFORMATION: DNA Primer

<400> SEQUENCE: 18
tctcacagat ggaggtgatg c                                                  21

<210> SEQ ID NO 19
<211> LENGTH: 20
<212> TYPE: DNA
<213> ORGANISM: Artificial sequence
<220> FEATURE:
<223> OTHER INFORMATION: DNA Primer

<400> SEQUENCE: 19
gggacatggt ttcaatcacc                                                    20

<210> SEQ ID NO 20
<211> LENGTH: 20
<212> TYPE: DNA
<213> ORGANISM: Artificial sequence
<220> FEATURE:
<223> OTHER INFORMATION: DNA Primer

<400> SEQUENCE: 20
tctggtacag actctggctg                                                    20

<210> SEQ ID NO 21
<211> LENGTH: 22
<212> TYPE: DNA
<213> ORGANISM: Artificial sequence
<220> FEATURE:
<223> OTHER INFORMATION: DNA Primer

<400> SEQUENCE: 21
ttacggctat gtcaccatcc tt                                                 22

<210> SEQ ID NO 22
<211> LENGTH: 20
<212> TYPE: DNA
<213> ORGANISM: Artificial sequence
<220> FEATURE:
<223> OTHER INFORMATION: DNA Primer

<400> SEQUENCE: 22
ccccaccagc aagtcatcca                                                    20
```

<210> SEQ ID NO 23
<211> LENGTH: 22
<212> TYPE: DNA
<213> ORGANISM: Artificial sequence
<220> FEATURE:
<223> OTHER INFORMATION: DNA Primer

<400> SEQUENCE: 23
cctcttccac aaatcagacg gc					22

<210> SEQ ID NO 24
<211> LENGTH: 22
<212> TYPE: DNA
<213> ORGANISM: Artificial sequence
<220> FEATURE:
<223> OTHER INFORMATION: DNA Primer

<400> SEQUENCE: 24 ctcttttca taaggggcag ca					22

<210> SEQ ID NO 25
<211> LENGTH: 23
<212> TYPE: DNA
<213> ORGANISM: Artificial sequence
<220> FEATURE:
<223> OTHER INFORMATION: DNA Primer

<400> SEQUENCE: 25
atcttggcaa aactagctca act				23

<210> SEQ ID NO 26
<211> LENGTH: 23
<212> TYPE: DNA
<213> ORGANISM: Artificial sequence
<220> FEATURE:
<223> OTHER INFORMATION: DNA Primer

<400> SEQUENCE: 26
cgactctctt tactaaacgg gac				23

<210> SEQ ID NO 27
<211> LENGTH: 21
<212> TYPE: DNA
<213> ORGANISM: Artificial sequence
<220> FEATURE:
<223> OTHER INFORMATION: DNA Primer

<400> SEQUENCE: 27
cgacacaccg agatcctaac a					21

<210> SEQ ID NO 28
<211> LENGTH: 20
<212> TYPE: DNA
<213> ORGANISM: Artificial sequence
<220> FEATURE:
<223> OTHER INFORMATION: DNA Primer

<400> SEQUENCE: 28
atatccagga ggtggcgttt					20

<210> SEQ ID NO 29
<211> LENGTH: 21
<212> TYPE: DNA
<213> ORGANISM: Artificial sequence
<220> FEATURE:

```
<223> OTHER INFORMATION: DNA Primer

<400> SEQUENCE: 29
taccagcgtt tggatctatg c                                              21

<210> SEQ ID NO 30
<211> LENGTH: 21
<212> TYPE: DNA
<213> ORGANISM: Artificial sequence
<220> FEATURE:
<223> OTHER INFORMATION: DNA Primer

<400> SEQUENCE: 30
gccggttcct attctgtctc g                                              21

<210> SEQ ID NO 31
<211> LENGTH: 21
<212> TYPE: DNA
<213> ORGANISM: Artificial sequence
<220> FEATURE:
<223> OTHER INFORMATION: DNA Primer

<400> SEQUENCE: 31
ctctctcttt ctggcctgga g                                              21

<210> SEQ ID NO 32
<211> LENGTH: 20
<212> TYPE: DNA
<213> ORGANISM: Artificial sequence
<220> FEATURE:
<223> OTHER INFORMATION: DNA Primer

<400> SEQUENCE: 32
tctgctggat gacgtgagta                                                20

<210> SEQ ID NO 33
<211> LENGTH: 52
<212> TYPE: DNA
<213> ORGANISM: Artificial sequence
<220> FEATURE:
<223> OTHER INFORMATION: DNA Primer

<400> SEQUENCE: 33
gtaataaagt caattaaaaa cttccgcgga tttctttgga cccaggaaac ag            52

<210> SEQ ID NO 34
<211> LENGTH: 42
<212> TYPE: DNA
<213> ORGANISM: Artificial sequence
<220> FEATURE:
<223> OTHER INFORMATION: DNA Primer

<400> SEQUENCE: 34
tccgcggatt tctttggact taagaaacag ccatgtgggt cc                       42

<210> SEQ ID NO 35
<211> LENGTH: 45
<212> TYPE: DNA
<213> ORGANISM: Artificial sequence
<220> FEATURE:
<223> OTHER INFORMATION: DNA Primer

<400> SEQUENCE: 35
gcactatgaa cgcttctttc cgtcgacaga aaatgtgtag tctac                    45
```

<210> SEQ ID NO 36
<211> LENGTH: 51
<212> TYPE: DNA
<213> ORGANISM: Artificial sequence
<220> FEATURE:
<223> OTHER INFORMATION: DNA Primer

<400> SEQUENCE: 36
gagttctcca ataaaaccaa tttccgcgga atatttgatg ttttccttg t    51

<210> SEQ ID NO 37
<211> LENGTH: 40
<212> TYPE: DNA
<213> ORGANISM: Artificial sequence
<220> FEATURE:
<223> OTHER INFORMATION: DNA Primer

<400> SEQUENCE: 37
gaagggaagg ccaacttctc gaggtctgga aggccaaagg    40

<210> SEQ ID NO 38
<211> LENGTH: 41
<212> TYPE: DNA
<213> ORGANISM: Artificial sequence
<220> FEATURE:
<223> OTHER INFORMATION: DNA Primer

<400> SEQUENCE: 38
ggttttccct gcagcgttac tagtgactta agagggcagg a    41

<210> SEQ ID NO 39
<211> LENGTH: 30
<212> TYPE: DNA
<213> ORGANISM: Artificial sequence
<220> FEATURE:
<223> OTHER INFORMATION: DNA Primer

<400> SEQUENCE: 39
caggcagcct ttccgcggcc agctgttgct    30

<210> SEQ ID NO 40
<211> LENGTH: 59
<212> TYPE: DNA
<213> ORGANISM: Artificial sequence
<220> FEATURE:
<223> OTHER INFORMATION: DNA Primer

<400> SEQUENCE: 40
agaatgtaag tgtttcgcct aggcccaaaa tcccttctcc gcggtaccgt cgtttctgg    59

<210> SEQ ID NO 41
<211> LENGTH: 22
<212> TYPE: DNA
<213> ORGANISM: Artificial sequence
<220> FEATURE:
<223> OTHER INFORMATION: DNA Primer

<400> SEQUENCE: 41
gcgagagtgc gggccccagg ag    22

<210> SEQ ID NO 42
<211> LENGTH: 21
<212> TYPE: DNA
<213> ORGANISM: Artificial sequence
<220> FEATURE:
<223> OTHER INFORMATION: DNA Primer

```
<400> SEQUENCE: 42
cacgatttgc gtgtcatcct t                                              21

<210> SEQ ID NO 43
<211> LENGTH: 22
<212> TYPE: RNA
<213> ORGANISM: Homo sapiens

<400> SEQUENCE: 43
cuccuggggc ccgcacucuc gc                                             22
```